(12) United States Patent
Neumann et al.

(10) Patent No.: US 8,470,306 B2
(45) Date of Patent: Jun. 25, 2013

(54) CROSSLINKED POLYSILOXANES, A PROCESS FOR THEIR PREPARATION AND USE OF THE CROSSLINKED POLYSILOXANES IN EMULSIFIER SYSTEMS FOR WATER-IN-OIL EMULSIONS

(75) Inventors: Thomas Neumann, Bochum (DE); Burghard Gruening, Essen (DE); Anna Howe, Moseley, VA (US); Dana Adkins, Quinton, VA (US); Jerry Reddinger, Chesterfield, VA (US)

(73) Assignee: Evonik Goldschmidt GmbH, Essen (DE)

( * ) Notice: Subject to any disclaimer, the term of this patent is extended or adjusted under 35 U.S.C. 154(b) by 5 days.

(21) Appl. No.: 12/888,603

(22) Filed: Sep. 23, 2010

(65) Prior Publication Data
US 2011/0070183 A1    Mar. 24, 2011

Related U.S. Application Data

(60) Provisional application No. 61/245,366, filed on Sep. 24, 2009.

(51) Int. Cl.
*A61K 31/74* (2006.01)
*C08G 77/04* (2006.01)

(52) U.S. Cl.
USPC ...................... 424/78.02; 525/474

(58) Field of Classification Search
USPC ...................... 424/78.02; 525/474
See application file for complete search history.

(56) References Cited

U.S. PATENT DOCUMENTS

| | | | |
|---|---|---|---|
| 3,715,334 A | 2/1973 | Karstedt | |
| 3,775,452 A | 11/1973 | Karstedt | |
| 4,096,159 A | 6/1978 | Hechtl et al. | |
| 4,698,178 A * | 10/1987 | Huttinger et al. | 516/23 |
| 5,147,965 A | 9/1992 | Ichinohe et al. | |
| 5,225,509 A | 7/1993 | Heinrich et al. | |
| 6,482,912 B2 | 11/2002 | Boudjouk et al. | |
| 8,211,972 B2 * | 7/2012 | Meyer et al. | 524/588 |
| 2003/0053970 A1 | 3/2003 | Bruening et al. | |
| 2004/0186259 A1 | 9/2004 | Brehm et al. | |
| 2004/0186260 A1 | 9/2004 | Hohenberg et al. | |
| 2005/0075468 A1 | 4/2005 | Knott et al. | |
| 2006/0041097 A1 | 2/2006 | Herrwerth et al. | |
| 2006/0155089 A1 | 7/2006 | Ferenz et al. | |
| 2006/0155090 A1 | 7/2006 | Ferenz et al. | |
| 2006/0241270 A1 | 10/2006 | Burkhart et al. | |
| 2007/0043193 A1 | 2/2007 | Henning et al. | |
| 2007/0100153 A1 | 5/2007 | Brueckner et al. | |
| 2007/0299231 A1 | 12/2007 | Doehler et al. | |
| 2008/0227923 A1 | 9/2008 | Klein et al. | |

FOREIGN PATENT DOCUMENTS

| | | |
|---|---|---|
| DE | 26 46 726 | 4/1978 |
| DE | 103 12 636 | 9/2004 |
| DE | 103 59 764 | 7/2005 |
| DE | 10 2005 001 039 | 7/2006 |
| DE | 10 2005 001 041 | 7/2006 |
| DE | 10 2005 051 939 | 5/2007 |
| DE | 10 2007 012 241 | 9/2008 |
| DE | 10 2008 001 788 | 11/2009 |
| EP | 0 513 645 | 11/1992 |
| EP | 1 439 200 | 7/2004 |
| EP | 1 460 098 | 9/2004 |
| EP | 1 520 870 | 4/2005 |
| EP | 1 627 892 | 2/2006 |
| EP | 1 754 740 | 2/2007 |
| JP | 1997-183710 A * | 7/1997 |
| JP | 2001-187711 A * | 7/2001 |
| JP | 2001-294753 A * | 10/2001 |
| JP | 2003-119389 A * | 4/2003 |
| JP | 2003-128518 A * | 5/2003 |

\* cited by examiner

*Primary Examiner* — Blessing Fubara
(74) *Attorney, Agent, or Firm* — Frommer Lawrence & Haug LLP

(57) ABSTRACT

The invention relates to crosslinked organopolysiloxanes which are linked by a polyether building block via the Si atoms, to emulsifier systems which have these crosslinked organopolysiloxanes, and also to cosmetic, dermatological or pharmaceutical formulations comprising a crosslinked organopolysiloxane or an emulsifier system comprising these.

17 Claims, No Drawings

CROSSLINKED POLYSILOXANES, A PROCESS FOR THEIR PREPARATION AND USE OF THE CROSSLINKED POLYSILOXANES IN EMULSIFIER SYSTEMS FOR WATER-IN-OIL EMULSIONS

This application claims benefit under 35 U.S.C. 119(e) of U.S. Provisional Application Ser. No. 61/245,366, filed on 24 Sep. 2009.

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

The present invention relates to crosslinked organopolysiloxanes which are linked by a polyether building block via the Si atoms, to emulsifier systems which have these crosslinked organopolysiloxanes, and also to cosmetic, dermatological or pharmaceutical formulations comprising a crosslinked organopolysiloxane or an emulsifier system comprising these.

Organomodified siloxanes are used in a very wide variety of applications. Their properties can be adjusted in a targeted manner, inter alia, by the type of modification, and also by the modification density.

Thus, for example, with allyl polyethers, organophilic or non-ionic hydrophilic groups can be bonded to a siloxane backbone. Thus, e.g. DE 102005001041 (U.S. Patent Appl. Publication 2006-155090) describes functionalized polyorganosiloxanes and their use as fuel defoamer. The allyl polyethers in the siloxanes presented there can, if appropriate, be replaced by hydrocarbon radicals by modifying the synthesis.

In general, siloxanes can be linked with oleophilic groups by reaction with e.g. α-olefins. The silicone waxes obtained in this way serve, for example, as additives in personal care applications.

It is found in many fields of application that the effect of the siloxane depends decisively on the compatibility with the corresponding formulation.

Suitable cosmetic emulsifiers are, for example, siloxanes which, besides aliphatic groups based on α-olefins, carry polyethers. A typical example to be mentioned here is the commercial product ABIL® EM 90 from Evonik Goldschmidt GmbH (Germany), which is characterized in particular by excellent stabilization of water-in-oil (W/O) emulsions (U.S. Pat. No. 4,698,178).

A disadvantage of this water-in-oil emulsifier is that its use in formulations which have a high fraction of silicone oil (>15% by weight), in particular a high fraction of cyclopentasiloxanes, does not lead to emulsions which are stable in the long term, possibly also at elevated temperature. In order that this is nevertheless possible, further coemulsifiers or emulsifier systems often have to be added to the known emulsifiers, such as e.g. ABIL® EM 90, or it is necessary to use formulations with a lower fraction of silicone oil. Further coemulsifiers/stabilizers are often also required for the stabilization of emulsions which comprise crystalline constituents, such as e.g. UV absorbers or waxes.

It was therefore an object of the present invention to provide alternative water-in-oil emulsifiers which enable stable emulsions to also be prepared from formulations with a relatively high fraction of silicone oil. Moreover, the water-in-oil emulsifier should preferably be suitable for making stable emulsions accessible which have crystalline constituents.

Surprisingly, it has been found that through the use of emulsifier systems which have a crosslinked organopolysiloxane according to claim 1, which has organopolysiloxane units linked by alkyl polyether building blocks, it is possible to prepare emulsions which are stable over several months also from formulations which have a fraction of silicone oil, in particular of cyclopentasiloxane, of more than 15% by mass.

The present invention therefore provides crosslinked organopolysiloxanes according to the claims and the subsequent description, the use of the crosslinked organopolysiloxanes according to the invention for the preparation of emulsifier systems and emulsifier systems which have these crosslinked organopolysiloxanes according to the invention, and also the use of at least one of the emulsifier systems according to the invention for the preparation of water-in-oil emulsions or dispersions.

The present invention likewise provides cosmetic or pharmaceutical water-in-oil emulsions or dispersions comprising at least one of the emulsifier systems according to the invention.

The present invention furthermore provides the use of the crosslinked organopolysiloxanes according to the invention or of the emulsifier systems according to the invention for the preparation of cosmetic, dermatological or pharmaceutical formulations, and also the corresponding cosmetic, dermatological or pharmaceutical formulations themselves.

The crosslinked organopolysiloxanes according to the invention have the advantage that they are suitable, on their own or preferably in mixtures with uncrosslinked organopolysiloxanes, as emulsifiers for the preparation of emulsions which have a high content of silicone oils and preferably meet one or more of the other requirements mentioned before.

The crosslinked organopolysiloxanes according to the invention have a considerably higher viscosity than uncrosslinked organopolysiloxanes as they are used in the prior art. This has the advantage that even during the preparation of the emulsions, higher viscosities arise, meaning that more efficient input of shear forces during emulsion formation is possible.

The crosslinked organopolysiloxanes according to the invention and/or the emulsifier systems prepared from them, moreover, have the advantage that they lead to emulsions which have good long-term stability.

A further advantage of the crosslinked organopolysiloxanes according to the invention and/or the emulsifier systems prepared from them is that they are able to stabilize liquids which have a tendency towards crystallization. The crosslinked organopolysiloxanes according to the invention and/or the emulsifier systems prepared from them thus suppress the formation of crystals.

The emulsifiers of the present invention have the advantage that they allow the production of water-in-oil emulsions that contain more than 80% by weight of a water phase and less than or equal to 1% by weight of an emulsifier.

With the emulsifier of the present invention it is possible to produce quick break water-in-oil emulsions, which break immediately after application to the skin and provide a distinct and visible moisturising effect.

The substances, mixtures and formulations according to the invention are described below by way of example without any intention of limiting the invention to these exemplary embodiments. Where ranges, general formulae or compound classes are given below, then these are intended to encompass not only the corresponding ranges or groups of compounds explicitly mentioned, but also all part ranges and part groups of compounds which can be obtained by removing individual values (ranges) or compounds. Where documents are cited within the context of the present description, then it is intended for their content, in its entirety, to form part of the disclosure of the present invention. If, within the context of the present invention, compounds such as, for example, organomodified polysiloxanes are described which can have different units a number of times, then these may occur in these compounds in random distribution (random oligomer) or arranged (block oligomer). Data relating to the number of units in such compounds is to be understood as meaning the average value, averaged over all of the corresponding compounds. Unless stated otherwise, all of the data in percent (%) are percent by mass. Unless stated otherwise, all of the average values which may be stated are number averages.

The crosslinked organopolysiloxanes according to the invention are characterized in that they have organopolysiloxane units linked by building blocks of the formula (I)

$$—CH_2—CH_2\text{-}(G)_nO(EO)_x(PO)_y(XO)_z— \qquad (I),$$

where
$G$=divalent organic radical, preferably $CH_2$, $C=O$, $CR^5_2$ or $CHR^5$, preferably $CH_2$,
$EO=C_2H_4O$
$PO=C_3H_6O$ (propylene oxide unit)
$XO=C_2H_3R^5O$
n=1 to 16, preferably 1 to 9 and more preferably 1
x=2 to 50, preferably 5 to 30, preferably from 6 to 15,
y=0 to 50, preferably 0 or >0 to 15, preferably 0,
z=0 to 10, preferably 0 or >0 to 2, preferably 0,
$R^5$=independently of one another, identical or different radicals selected from the group comprising alkyl radicals having 2 to 16 carbon atoms, which are optionally interrupted by ether functions, alkaryl radicals having 7 to 18 carbon atoms, aryl radicals having 6 to 16 carbon atoms, preferably ethyl or phenyl, where the building blocks of the formula (I) are directly linked to an Si atom at both linkage points.

The compounds according to the invention are present in the form of a mixture with a distribution controlled essentially by laws of statistics. The values for the indices x, y and z are therefore average values. The units characterized with the indices x, y and z can be present in the compounds of the formula II in random distribution, blockwise or arranged in any other desired order.

Preferably, each linked organopolysiloxane unit has, on average, more than 1, preferably from 1 to 10, preferably from 1.1 to 5 and particularly preferably from 1.5 to 4, linkage points to a building block of the formula I.

In the crosslinked organopolysiloxanes according to the invention, the organopolysiloxane units are preferably identical or different units of the formula (II)

$$M_{2+c+2d}D_aD'_bT_cQ_d \qquad (II)$$

where
$M=(R^1R^2_2SiO_{1/2})$
$D=(R^2_2SiO_{2/2})$
$D'=(R^2R^3SiO_{2/2})$
$T=(R^2SiO_{3/2})$
$Q=(SiO_{4/2})$
a=30 to 800, preferably 40 to 500, preferably 50 to 400, particularly preferably 75 to 150,
b=1 to 40, preferably 3 to 35, preferably 20 to 30,
c=0 to 2, preferably 0 or >0 to 1, preferably 0.05 to 0.2, particularly preferably about 0.1,
d=0 to 2, preferably 0 or >0 to 1, preferably 0,
$R^1=R^2$ or $R^3$, $R^2$=independently of one another, V or H or identical or different linear or branched, optionally aromatic hydrocarbon radicals having 1 to 32, preferably 6 to 25, carbon atoms, which optionally carry OH or ester functions, preferably $C_9$-, $C_{12}$-, $C_{16}$- or $C_{22}$-hydrocarbon radical or methyl radical or phenyl radical, in particular methyl radical,
$R^3$=independently of one another, identical or different polyether radicals of the general formula (III)

$$—CH_2—CH_2—(G)_nO(EO)_x(PO)_y(XO)_zR^4 \qquad (III)$$

where
$G$=divalent organic radical, preferably $CH_2$, $C=O$, $CR^5_2$ or $CHR^5$, preferably $CH_2$,
$EO=(—C_2H_4O—)$
$PO=(—C_9H_6O—)$
$XO=(C_2H_3R^5O)$
n=1 to 16, preferably 1 to 9 and more preferably 1
x=2 to 50, preferably 5 to 30, preferably from 6 to 15,
y=0 to 50, preferably 0 or >0 to 15, preferably 0,
z=0 to 10, preferably 0 or >0 to 2, preferably 0,
$R^4$=independently of one another, identical or different radicals selected from the group comprising H, alkyl radicals having 1 to 16 carbon atoms, or carboxylate radicals, preferably comprising 2 to 22 carbon atoms, and
$R^5$=independently of one another, identical or different radicals selected from the group comprising alkyl radicals having 2 to 16 carbon atoms, which are optionally interrupted by ether functions, alkaryl radicals having 7-18 carbon atoms and aryl radicals having 6 to 16 carbon atoms, preferably ethyl or phenyl, and
V=a bond (a linkage point) to the building block of the formula I,
where at least one V is present per organopolysiloxane unit (II). Preferably, radical $R^2$ is a bond V only in the units M and D. The radical $R^2$ is preferably not a hydrogen atom.

The average number of linkage points V per unit of formula (II) is preferably more than or equal to 1, preferably 1 to 5 and more preferably 1 to 2.

It may be advantageous if, on average, at least one building block (I) is attached via an SiOC bond in the crosslinked organopolysiloxane according to the invention per organopolysiloxane unit of the formula (II). It may also be advantageous if, on average, at least one building block (I) is attached via an SiC bond in the crosslinked organopolysiloxane according to the invention per organopolysiloxane unit of the formula (II). It may be particularly advantageous if on average at least one building block (I) is attached via an SiOC bond and at least one building block (I) is attached via an SiC bond in the crosslinked organopolysiloxane according to the invention per organopolysiloxane unit of the formula (II), where the building block (I) is preferably not identical, i.e. a building block (I) is not bonded with an SiOC and an SiC bond at only one organopolysiloxane unit of the formula (II).

The crosslinked organopolysiloxane according to the invention and/or the emulsifier system according to the invention preferably has an HLB value of from 4 to 10, preferably from 6 to 8.

The crosslinked organopolyethersiloxanes according to the invention can be prepared in a very wide variety of ways. Preferably, the starting compounds used are identical or different organopolysiloxanes of the formula (IIa)

$$M_{2+c+2d}D_aD'_bT_cQ_d \qquad (IIa)$$

where the abbreviations have the meanings given above for formula (II), with the proviso that $R^2$ may be a hydrogen instead of V. Preferably, the radical $R^2$ is a hydrogen only in the units M and/or D.

Preferably, the preparation of the crosslinked organopolysiloxanes according to the invention takes place with the process according to the invention for the preparation of a crosslinked organopolysiloxane, which is characterized in that identical or different organopolysiloxanes of the formula (IIa), where the indices and abbreviations have the meanings given for formula (II), with the proviso that $R^2$ may be a hydrogen instead of V and/or is at least one hydrogen, are reacted in a hydrosilylation reaction with a compound which has at least one hydroxy group and at least one multiple bond, and optionally compounds which have at least one multiple bond and no OH group. Preferably, the reaction conditions are chosen such that, following the hydrosilylation, some of the Si—H bonds are furthermore present in the reaction product, and a dehydrogenative condensation is carried out with the resulting reaction product.

The average number of SiH bonds per organopolysiloxane of the formula (IIa) is preferably more than or equal to 1, preferably 1 to 5 and more preferably 1 to 2.

Compounds which can be used as SiH-functional siloxanes of the formula (IIa) in the process according to the invention can be obtained e.g. by an equilibration of various siloxane basic bodies. Processes for the equilibration are described, for example, in the patent specifications EP 1439200 (U.S. Patent Appl. Publication 2006-241270) and DE 102005001039 (U.S. Patent Appl. Publication 2006-155089), to which reference is expressly made and which are thus part of the disclosure of the present application. On an industrial scale, to synthesize SiH-group-carrying organopolysiloxanes, preferably readily accessible siloxane compounds, such as, for example, octamethylcyclo-tetrasiloxane, decamethylcyclopentasiloxane, poly(methyl hydrogen)siloxanes, 1,1,3,3-tetramethyldisiloxane or hexamethyldisiloxane, are reacted in the presence of a suitable catalyst. Suitable catalysts are strong acids, such as e.g. trifluoromethanesulphonic acid. In the process, the corresponding equilibrates are formed. The SiH functionalities can be present, depending on the catalyst used, in random distribution over the siloxane main chain, or else may occur blockwise. The degree of functionality of the individual polymer molecules is also subject to a distribution. The indices a, b, c and d of the siloxanes used in the context of this invention are therefore average values. The units characterized with the indices a, b, c and d can be present in the compounds of the formula IIa in random distribution, blockwise or arranged in any other desired order.

The organopolysiloxanes of the formula (IIa) are reacted with a compound which has at least one hydroxy group and at least one, preferably terminal, multiple bond, in particular double bond. Preference is given to using compounds of the formula (IIIa)

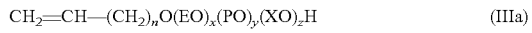

$$CH_2=CH-(CH_2)_nO(EO)_x(PO)_y(XO)_zH \qquad (IIIa)$$

where the symbols, abbreviations and indices have the meaning given for formula (III).

The compounds of the formula (IIIa) can be prepared by the addition reaction of alkoxides onto monofunctional alcohols which have at least one vinyl group. On account of their good commercial availability, of suitability for the synthesis of polyethers are in particular the alkoxides: ethylene oxide, propylene oxide, butylene oxide or styrene oxide.

If different monomers are used for the preparation of the polyethers, for example in order to adjust the hydrophilicity of the product in a targeted manner, then it is possible, by means of the order of the metered addition and by means of the adjustment of various reaction parameters, to control the distribution of the monomer units along the polyether main chain so that, for example, different monomer units can arise blockwise or be present in gradual and/or random distribution.

It may be advantageous if the organopolysiloxanes of the formula (IIa) are reacted (in one process step) simultaneously or in succession, preferably simultaneously to the reaction with compounds which have at least one hydroxy group and at least one, preferably terminal, multiple bond, in particular double bond, preferably compounds of the formula (IIIa), compounds which have at least one, preferably at least one terminal, multiple bond, in particular double bond and no OH group. Preferably used compounds are those of the formula (IIId)

$$CH2=CR^6-R^7 \qquad (IIId)$$

where $R^6$=H or branched or unbranched, preferably unbranched, alkyl radical having 1 to 10 carbon atoms, preferably H, and $R^7$=H or a branched or unbranched, preferably unbranched, alkyl radical or an aryl, arylalkyl or alkaryl radical having in each case 1 to 30 carbon atoms. Preferred compounds of the formula (IIId) are alpha-olefins having on average 2 to 32, preferably 6 to 25, and preferably 9, 12, 16 or 22 carbon atoms.

In the reaction, the ratio of compounds of the formula (IIa) to the specified compounds, in particular the compounds of the formula (IIIa) and optionally of (IIId), is preferably chosen such that the sum of the number of OH equivalents and double bond equivalents in the compounds of the formula (IIIa) and (IIId) exceeds the number of Si—H bond equivalents in the compounds of the formula IIa. Preferably, the ratio of the sum of OH equivalents and double bond equivalents to Si—H bond equivalents is from 6:1 to 1.1:1, particularly preferably from 2:1 to 1.2:1. It is, however, also possible to carry out the reaction with a ratio of less than or equal to 1:1.

In the reaction, at least one hydrosilylation, which leads, with reaction of the vinyl bond with the Si—H bond, to the formation of SiC bonds, and one dehydrogenative condensation in which SiOC bonds are formed with the reaction of the OH group with the SiH bond, is carried out.

The conversion with the two reactions can be carried out in one step or in a plurality of steps. Preferably, the conversion takes place in a plurality of steps, in particular in two steps. In the conversion in two steps, the hydrosilylation can firstly be carried out, followed by the dehydrogenative condensation, or vice versa. Preferably, the hydrosilylation is firstly carried out followed by the dehydrogenative condensation.

The hydrosilylation and the dehydrogenative condensation can be carried out in a manner known to the person skilled in the art.

Possible hydrosilylation processes which can be used are described e.g. in Bogdan Marciniec, "Comprehensive Handbook on Hydrosilylation", Pergamon Press 1992; Iwao Ojima, "The hydrosilylation reaction" in "The chemistry of organic silicon compounds" (Editors S. Patai and Z. Rappoport), Wiley 1989, in EP 1754740 (U.S. Patent Appl. Publication 2007-043193), "Chemie and Technologie der Silicone [Chemistry and Technology of Silicones]", Verlag Chemie, 1960, page 43 ff., and in DE 2646726 (U.S. Pat. No. 4,096,159), U.S. Pat. No. 3,775,452 and EP 1520870 (U.S. Patent Appl. Publication 2005-075468), and in Iwao Ojima et al., "Recent advances in the hydrosilylation and related reactions" in "The chemistry of organic silicon compounds, Vol. 2" (Editors Z. Rappoport and Y. Apeloig), Wiley 1998, to which reference is expressly made and the content of which forms part of the disclosure of the present application.

The catalysts used for the hydrosilylation reaction are preferably platinum and its compounds. Here, the platinum is used either in metallic form, as metal fixed to a support or in the form of an optionally soluble platinum complex. To date, the majority of hydrosilylation reactions carried out industrially are carried out using the so-called Karstedt catalyst known from U.S. Pat. No. 3,715,334 and U.S. Pat. No. 3,775,452, which is also the preferred catalyst for carrying out the hydrosilylation reaction in the present invention.

Preferably, the catalyst is used in an amount of from 5 to 20 ppm by mass of a platinum or rhodium catalyst (mass fraction of noble metal based on the mass of the total mixture). The catalyst is particularly preferably used in the form of hexachloroplatinic acid, cis-platinum, di-μ-chloro-bis[chloro(cyclohexene)platinum(II)] or Karstedt catalyst (optionally dissolved in solvents), or in the form of finely divided elemental platinum on a support material such as aluminium oxide, silica gel or activated carbon. The hydrosilylation is preferably carried out at a temperature of from 60 to 200° C., preferably from 70 to 130° C. Preferably, the hydrosilylation is carried out at a pressure of from 0.9 to 20 bar, preferably at 0.980 to 2 bar.

The hydrosilylation reaction can take place without a solvent or in the presence of solvents. Carrying out the hydrosilylation reaction in the presence of a solvent, however, may be advantageous since the polyether compounds of the formula IIIa used are immiscible or only poorly miscible with the compounds of the formula IIa. By choosing a suitable solvent in which both the compound of the formula IIIa and also the compound of the formula IIa are at least partially soluble, it is possible to achieve a more rapid start to the reaction and/or a higher reaction rate. Preference is given to using inert solvents, such as, for example, xylene or toluene. The hydrosilylation reaction is particularly preferably carried out without solvents.

The technical procedure for the preparation of the polyethersiloxanes can influence the properties of the product, particularly if a plurality of different polyether radicals are added on. The hydrosilylation can be operated discontinuously, semicontinuously or continuously. The hydrosilylation is preferably carried out discontinuously.

A dehydrogenative condensation is described, for example, in the book "Silicone Chemie and Technologie [Silicone Chemistry and Technology]", Vulkan-Verlag Essen, 1989, and in the specifications EP 1 460 098 (U.S. Patent Appl. Publication 2004-186259), DE 103 12 636 (U.S. Patent Appl. Publication 2004-186260), DE 103 59 764 (U.S. Patent Appl. Publication 2007-299231), DE 10 2005 051 939 (U.S. Patent Appl. Publication 2007-100153) and EP 1 627 892 (U.S. Patent Appl. Publication 2006-041097) and also in JP 48-19941, to which U.S. Pat. No. 5,147,965 refers. Reference is expressly made to the content of the cited specifications and the content of the cited specifications forms part of the disclosure of the present application.

The dehydrogenative condensation is preferably carried out in the presence of a catalyst. Suitable catalysts for the dehydrogenative condensation are, for example, NaOH, KOH, tetramethylammonium hydroxide, alkali metal fluorides, alkaline earth metal fluorides, boron catalysts, such as e.g. tris(pentafluorophenyl)borane, carboxylic acids, triflates, such as e.g. scandium triflate, and/or carboxylates or mixtures thereof. Preferred catalysts are those described e.g. in DE 103 12 636 and U.S. Pat. No. 6,482,912.

The catalysts used are preferably elemental compounds of main group III and/or elemental compounds of the third subgroup. Preferred catalysts are boron- and/or aluminium-containing catalysts and/or scandium-, yttrium-, lanthanum- and/or lanthanoid-containing catalysts.

The boron catalysts used are preferably $(C_5F_4)$ $(C_6F_5)_2B$; $(C_5F_4)_3B$; $(C_6F_5)BF_2$; $BF(C_6F_5)_2$; $B(C_6F_5)_3$; $BCl_2(C_6F_5)$; $BCl(C_6F_5)_2$; $B(C_6H_5)$ $(C_6F_5)_2$; $B(Ph)_2(C_6F_5)$; $[C_6H_4(mCF_3)]_3$ B; $[C_6H_4(pOCF_3)]_3B$; $(C_6F_5)B(OH)_2$; $(C_6F_5)_2BOH$; $(C_6F_5)_2$ BH; $(C_6F_5)BH_2$; $(C_7H_{11})B(C_6F_5)_2$; $(C_8H_{14}B)(C_6F_5)$; $(C_6F_5)_2B(OC_2H_5)$; $(C_6F_5)_2B-CH_2CH_2Si(CH_3)_3$;

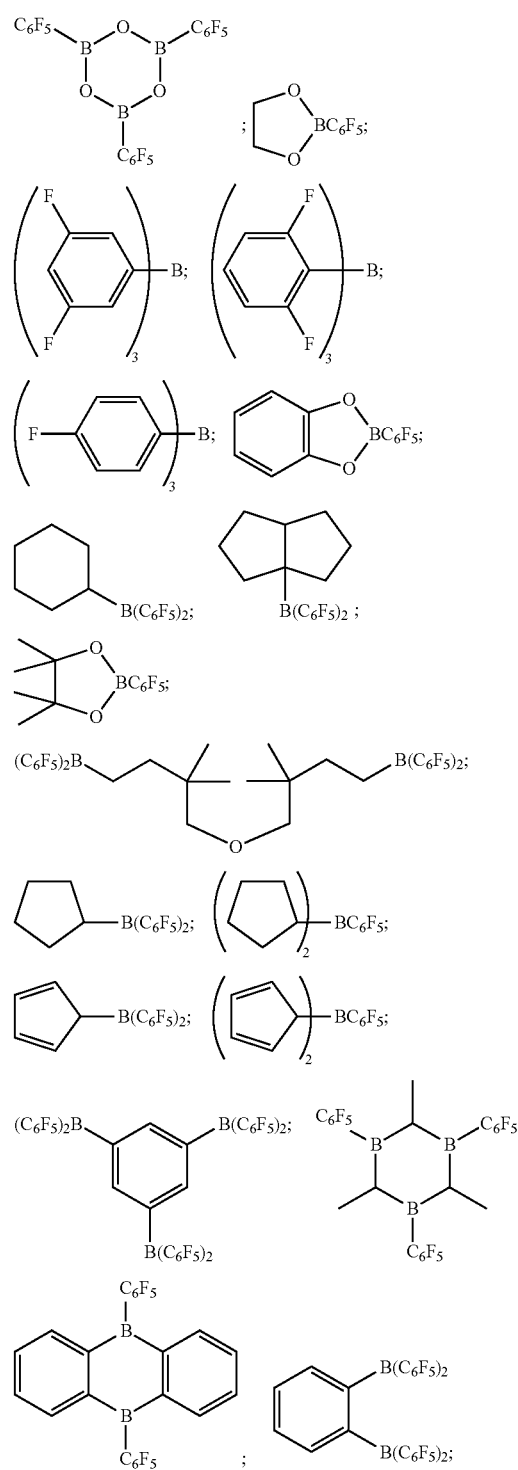

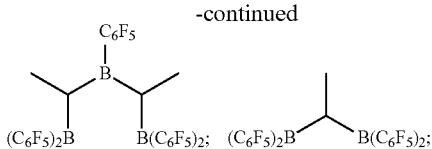

(C₆F₅)₂B   B(C₆F₅)₂;   (C₆F₅)₂B   B(C₆F₅)₂;

in particular tris(perfluorotriphenylborane), boron trifluoride etherate, boranetriphenylphosphine complex, triphenylborane, triethylborane and boron trichloride, tris(pentafluorophenyl)boroxine (9Cl), 4,4,5,5-tetramethyl-2-(pentafluorophenyl)-1,3,2-dioxaborolane (9Cl), 2-(pentafluorophenyl)-1,3,2-dioxaborolane (9Cl), bis(pentafluorophenyl)cyclohexylborane, di-2,4-cyclopentadien-1-yl (penta-fluorophenyl)borane (9Cl), (hexahydro-3a(1H)-pentalenyl)bis(pentafluorophenyl)borane (9Cl), 1,3-[2-[bis(pentafluorophenyl)boryl]ethyl]tetramethyldisiloxane, 2,4,6-tris(pentafluorophenyl)borazine (7Cl, 8Cl, 9Cl), 1,2-dihydro-2-(pentafluorophenyl)-1,2-azaborine (9Cl), 2-(pentafluorophenyl)-1,3,2-benzodioxaborole (9Cl), tris(4-trifluoromethoxyphenyl)borane, tris(3-trifluoromethylphenyl)-borane, tris(4-fluorophenyl)borane, tris(2,6-difluorophenyl)borane, tris(3,5-difluorophenyl)borane, methylium triphenyl-tetrakis(pentafluorophenyl)borate, N,N-dimethylanilinium tetrakis(pentafluorophenyl)borate, and mixtures thereof.

Preferred catalysts which do not contain boron are selected from: AlCl₃, aluminium acetylacetonate, AlF₃, aluminium trifluoromethanesulphonate, diisobutylaluminium chloride, di-isobutylaluminium hydride, triethylaluminium, scandium(III) chloride, scandium(III) fluoride, scandium(III) hexafluoroacetylacetonate, scandium(III) trifluoromethanesulphonate, tris(cyclopentadienyl)scandium, tris(cyclopentadienyl)yttrium, yttrium(III) chloride, yttrium(III) fluoride, yttrium(III) hexafluoroacetylacetonate, yttrium(III) naphthenate, lanthanum(III) chloride, lanthanum(III) fluoride, lanthanum(III) iodide, lanthanum(III) trifluoromethanesulphonate, tris(cyclopentadienyl)-lanthanum, cerium(III) bromide, cerium(III) chloride, cerium(III) fluoride, cerium(IV) fluoride, cerium(III) trifluoroacetylacetonate, tris(cyclopentadienyl)cerium, europium(III) fluoride, europium(II) chloride, praesodymium(III) hexafluoroacetylacetonate, praesodymium(III) fluoride, praesodymium(III) trifluoroacetylacetonate, samarium(III) chloride, samarium(III) fluoride, samarium(III) naphthenate, samarium(III) trifluoroacetylacetonate, ytterbium(III) fluoride, ytterbium(III) trifluoromethanesulphonate and tris(cyclopentadienyl)ytterbium, and mixtures thereof.

It is likewise possible to carry out the dehydrogenative condensation in the presence of the catalysts used in the hydrosilylation, in which case only very low reaction rates are achieved. Particular preference is given to using tris(pentafluorophenyl)borane or scandium(III) trifluoromethanesulphonate as catalyst.

The dehydrogenative condensation can be operated discontinuously, semicontinuously or continuously. The dehydrogenative condensation is preferably carried out discontinuously. The dehydrogenative condensation is preferably carried out without the use of solvent at a temperature of from 95 to 130° C., preferably at a temperature of about 110° C. The progression of the reaction can take place by continuously measuring the viscosity of the reaction mixture (in-process viscosity measurements).

The dehydrogenative condensation is preferably carried out after the hydrosilylation. It may be advantageous to remove the hydrosilylation catalyst from the reaction mixture before carrying out the dehydrogenative condensation. In order to keep the expenditure as low as possible, the hydrosilylation catalyst, however, preferably remains in the reaction mixture and, if desired, only the catalyst for the dehydrogenative condensation is replenished.

It may be advantageous if the reaction mixture from the hydrosilylation is treated prior to carrying out the dehydrogenative condensation by means of a deodorization, hydration and/or filtration. These work-up steps can be carried out as described in the prior art, e.g. in DE 10 2007 012 241 (U.S. Patent Appl. Publication 2008-227923) or EP 0 513 645 (U.S. Pat. No. 5,225,509).

The progression of the dehydrogenative condensation is preferably determined by measuring the viscosity of the reaction mixture. The dehydrogenative condensation can be terminated in various ways. If e.g. tetramethylammonium hydroxide is used as catalyst, the termination can be achieved by bringing the reaction mixture to an elevated temperature for a certain time (further details on this can be found in DE 10 2005 051 939). If boron catalysts, such as e.g. tris(pentafluorophenyl)borane, are used, then the reaction mixture can e.g. be diluted to terminate the reaction. To terminate the reaction, the reaction mixture is preferably diluted by at least 50% by volume, preferably from 75 to 150% by volume and particularly preferably by about 100% by volume. The diluents used are preferably the compounds obtained during the hydrosilylation reaction (compounds of the formula (IIb)). If the catalysts used for the hydrosilylation are also used in the dehydrogenative condensation, then, to terminate the reaction, suitable compounds, such as e.g. amine compounds, such as e.g. triisopropanolamine, triethanolamine, dimethylethanolamine, or methyldiethanolamine can be added to the reaction mixture. To terminate the reaction by adding amine compounds, preferably from 10 to 1000 ppm by mass (wppm), preferably 25 to 100 wppm and particularly preferably about 50 wppm, of amine compound are added to the reaction mixture.

Boron catalysts, in particular tris(pentafluorophenyl)borane, are preferably used in the dehydrogenative condensation. The content of boron catalyst based on the total weight of the reaction mixture is preferably from 10 to 5000 ppm by mass (wppm), preferably 25 to 1000 wppm and particularly preferably 50 to 250 wppm. When using boron catalysts, the reaction time is preferably from 1 to 20 h, preferably 2 to 17 h and particularly preferably 3 to 15 h.

It may be advantageous to free the reaction mixture from the dehydrogenative condensation from coarse impurities by a filtration, e.g. over filter plates.

In order to obtain preferred emulsifier systems according to the invention, the reaction preferably takes place such that firstly compounds of the formula (IIa) are reacted with compounds of the formula (IIIa) and optionally compounds (IIId) in a hydrosilylation reaction, where at most 99%, preferably from 80 to 98%, preferably 85% to 96% and particularly preferably 92 to 96%, of the SiH functions present are reacted with the multiple bonds of the compounds of the formula IIIa and optionally the compounds (IIId), and then some or all of the remaining SiH functions are reacted with the OH functions of the attached compounds of the formula IIIa. In order to obtain the aforementioned radicals on SiH functions, it may be advantageous to use the compounds of the formula IIIa in a corresponding deficiency based on the number of SiH functions present, or to terminate the hydrosilylation reaction.

During the dehydrogenative condensation, the reaction conditions are preferably chosen such that, after the end of the dehydrogenative condensation, at least 10%, preferably 20 to 75% and preferably 30 to 50%, of the Si—H bonds present after the hydrosilylation are still present.

The crosslinked organopolysiloxanes according to the invention can be used e.g. as emulsifiers or emulsifier system and/or for the preparation of emulsifier systems, in particular as emulsifiers and/or emulsifier systems for the preparation of water-in-oil emulsions. Accordingly, the present invention also provides these emulsifier systems.

The emulsifier systems according to the invention, in particular for cosmetic and pharmaceutical water-in-oil emulsions, preferably comprise the crosslinked organopolysiloxanes according to the invention.

Besides the crosslinked polysiloxanes, the emulsifier system according to the invention also preferably comprises uncrosslinked polysiloxanes of the formula (IIb), $$M_{2+c+2d}D_aD'_bT_cQ_d \quad \text{(IIb)}$$

where the meanings of the indices correspond to those given for formula II, with the proviso that $R^2$ is not V. $R^2$ can instead be a hydrogen or a radical $$CH_2=CH-(CH_2)_nO(EO)_x(PO)_y(XO)_z \quad \text{(IIIb), or}$$

$$-CH_2-CH_2-(CH_2)_nO(EO)_x(PO)_y(XO)_zH \quad \text{(IIIc)}$$

where the meaning of the indices and symbols correspond to that stated for formula III. Preferably, the compounds of the formula IIb have, on average, less than 5, preferably less than 2, hydrogen atoms bonded directly to silicon atoms per molecule. The uncrosslinked polysiloxanes IIb are preferably mixed hydrocarbon-polyethersiloxanes.

In the emulsifier system according to the invention, the mass ratio of crosslinked polysiloxanes II to uncrosslinked polysiloxanes IIb is preferably from 1:0 to 0.001:0.999, preferably from 0.99:0.01 to 0.01:0.99, more preferably 0.8:0.2 to 0.2:0.8, and particularly preferably from 0.6:0.4 to 0.4:0.6.

When the emulsifier systems according to the invention consist exclusively of crosslinked polysiloxanes and uncrosslinked polysiloxanes of the formula IIb and optionally the catalyst systems used in the preparation, they have a viscosity of from 800 to 15 000 mPas, preferably from 900 to 10 000 mPas and particularly preferably from 1000 to 8000 mPas.

Polyether radicals or building blocks of the formulae I or III in which $x/(1+y+z)$ is greater than 1, preferably 2 to 100 and particularly preferably from 5 to 30, are preferably present, preferably exclusively present, in the compounds of the formulae II and/or IIb of the emulsifier systems according to the invention.

It may be advantageous for the emulsifying properties and the skin feel if the fraction of unmodified D units ($Si(CH_3)_2O_{1/2}$) in the polyethersiloxanes used is significantly greater than the fraction of modified D' units. In the compounds of the formulae II and/or IIb, the ratio a/b is therefore preferably greater than 1, preferably >1.5 and particularly preferably >2 to <10.

It may be particularly advantageous for the skin feel if polyethersiloxanes with a relatively low polyether fraction are used. It may therefore be advantageous if, on average, at least three polyether radicals are present in the emulsifier systems according to the invention in the compounds of the formulae II and/or IIb, and the maximum number of polyether radicals $R^3$ bonded to the molecule is less than or equal to b.

The emulsifier system according to the invention preferably has a polydispersity of >10, preferably from 15 to 250, preferably from 50 to 250.

The polydispersity D is the quotient of the weight-average Mw and the number-average Mn of the molecular weight distribution of the polysiloxanes. The polydispersity is a recognized measure of the width of a molecular mass distribution. Polysiloxanes, in particular uncrosslinked polysiloxanes, typically have a polydispersity of D of less than 15.

A customary method for ascertaining the molecular weight distribution is gel permeation chromatography (GPC).

A GPC method in accordance with the standard DIN 55672-1/ISO 13885-1 was used. The GPC data were obtained on an Agilent 1100 system with autosampler and RI detector and the following parameters:

| | |
|---|---|
| Columns: | SDV 1000/10 000 Å and precolumn, |
| Length: | 65.00 cm, |
| Internal diameter: | 0.80 cm, |
| Temperature: | 30° C. |
| Mobile Phase: | THF |
| Flow rate: | 1.00 ml/min |
| Sample concentration: | 10.00 g/l |
| Calibration: | against PS [162-2057000 g/mol]. |

To evaluate the chromatograms, the evaluation software WinGPC Unity from Polymer Standards Service, Mainz, Germany, was used.

For the present data, only the product signal in the GPC chromatogram was taken into consideration. If the polysiloxanes are polyethersiloxanes which have been prepared by means of hydrosilylation, these usually comprise, as secondary constituent, a certain fraction of free polyether and/or unsaturated hydrocarbons and/or organic compounds. In the GPC these generate signals which in some cases superimpose the product peak. Accordingly, a standard multipeak evaluation analogous to HPLC evaluations was used and only the product signal (of the products formed by hydrosilylation) was taken into consideration. If other signals at relatively low molecular masses have superimposed this product signal, the minimum between the signals was determined using the evaluation software, a drop to the base line was carried out and only above the molecular weight of the minimum was the chromatogram in respect of relatively large molecular masses evaluated.

One preferable emulsifier system according to the invention, in particular for cosmetic and pharmaceutical water-in-oil emulsions, is characterized in that it has an HLB value of from 4 to 10, preferably 6 to 8, a polydispersity of >50, preferably 60 to 250 and a mass ratio of crosslinked polysiloxanes, preferably crosslinked polysiloxanes of formula II to uncrosslinked polysiloxanes, preferably uncrosslinked polysiloxanes of formula IIb of from 0.01:0.99 to 0.99:0.01, preferably from 0.8:0.2 to 0.2:0.8.

For the use of the emulsifier systems according to the invention in cosmetic applications, it is advantageous if these are liquid and pumpable at room temperature.

It is therefore advantageous to convert highly viscous emulsifier systems according to the invention into a pumpable, liquid form by adding suitable liquefying agents. Typically, pumpable systems of this type have a viscosity of <10 000 mPas (at a shear rate of 10 s$^{-1}$ at 25° C.). These pumpable liquefier-containing emulsifier systems are preferably clear to translucent-opaque.

Suitable liquefying agents which can be used are usually all types of cosmetic emollients. Cosmetic emollients which can be used are all cosmetic oils, in particular mono- or diesters of linear and/or branched mono- and/or dicarboxylic acids having 2 to 44 carbon atoms with linear and/or branched saturated or unsaturated alcohols having 1 to 22 carbon atoms. The esterification products of aliphatic, difunctional alcohols having 2 to 36 carbon atoms with monofunctional aliphatic carboxylic acids having 1 to 22 carbon atoms are likewise suitable. Also suitable are long-chain aryl acid esters such as e.g. esters of benzoic acid, e.g. benzoic acid esters of linear or branched, saturated or unsaturated alcohols having 1 to 22 carbon atoms, or else isostearyl benzoate or octyldodecyl benzoate. Further monoesters suitable as emollients and oil components are e.g. the methyl esters and isopropyl esters of fatty acids having 12 to 22 carbon atoms, such as e.g. methyl laurate, methyl stearate, methyl oleate, methyl erucate, isopropyl palmitate, isopropyl myristate, isopropyl stearate, isopropyl oleate. Other suitable monoesters are e.g. n-butyl stearate, n-hexyl laurate, n-decyl oleate. Suitable dicarboxylic acid esters are, for example, di-n-butyl adipate, di-n-butyl sebacate or di(2-ethylhexyl)adipate. Further fatty acid esters which can be used as emollients are, for example, $C_{12-15}$ alkyl benzoate, dicaprylyl carbonate, diethylhexyl carbonate. Emollients and oil components which may likewise be used are relatively long-chain triglycerides, i.e. triple esters of glycerol with three acid molecules, of which at least one is relatively long-chain. Mention may be made here, by way of example, of fatty acid triglycerides; as such, it is possible to use, for example, natural, vegetable oils, e.g. olive oil, sunflower oil or soybean oil and also synthetic triglycerides of caprylic/capric acid mixtures, triglycerides of technical-grade oleic acid, triglycerides with isostearic acid, or from palmitic acid/oleic acid mixtures as emollients and oil components. Furthermore, hydrocarbons, in particular also liquid paraffins and isoparaffins, can be used. Examples of hydrocarbons which can be used are paraffin oil, isohexadecane, polydecene, vaseline, paraffinum perliquidum, squalan, ceresine.

Mono- or polyhydric alcohols can also be used as liquefying agents. Such alcohols are, for example, ethanol, isopropyl alcohol or polyols. Polyols which are suitable here can have 2 to 15 carbon atoms and at least two hydroxyl groups. Typical examples are:

glycerol, alkylene glycols, such as, for example, ethylene glycol, diethylene glycol, 1,2- or 1,3-propylene glycol.

The invention therefore further provides liquid, pumpable emulsifier systems which comprise a liquefying agent as additional component.

These emulsifier systems are preferably clear to translucent-opaque.

The emulsifier systems according to the invention can be used as water-in-oil emulsifiers for the preparation of cosmetic and pharmaceutical water-in-oil emulsions. They can therefore also be used as dispersion auxiliaries for particles and pigments and consequently for the preparation of dispersions.

Suitable particles and pigments to be dispersed are, for example, finely disperse metal oxides and salts, such as, for example, titanium dioxide, zinc oxide, iron oxide, aluminium oxide, cerium oxide, zirconium oxide, silicates (talc), barium sulphate and zinc stearate. The particles here should have an average diameter of less than 1000 nm, preferably less than 100 nm, e.g. between 5 and 50 nm and in particular between 15 and 30 nm. They can have a spherical shape, although it is also possible to use those particles which have an ellipsoidal shape or a shape which deviates in some other way from the spherical form. Particles and pigments can moreover be micronized organic pigments, such as, for example, 2,2'-methylenebis{6-(2H-benzotriazol-2-yl)-4-(1,1,3,3-tetramethylbutyl)phenol} with a particle size of <200 nm. Furthermore, particles and pigments which lead to special sensory effects can also be dispersed in, such as, for example, nylon-12, boron nitride, polymer particles such as, for example, polyacrylate or polymethylacrylate particles or silicone elastomers.

The emulsifier systems according to the invention can be used for the preparation of water-in-oil emulsions or dispersions. Corresponding cosmetic or pharmaceutical water-in-oil emulsions or dispersions accordingly comprise at least one of the emulsifier systems according to the invention.

The crosslinked organopolysiloxanes according to the invention and the emulsifier systems according to the invention can be used for the preparation of cosmetic, dermatological or pharmaceutical formulations. Corresponding cosmetic, dermatological or pharmaceutical formulations which have the crosslinked organopolysiloxanes and/or the emulsifier systems are likewise provided by the present invention.

The cosmetic and pharmaceutical emulsions and dispersions according to the invention comprise, based on the total mass, more mass percent of oil component than the sum of the mass percents of emulsifier and optionally coemulsifier.

The invention further provides the use of the emulsifier systems according to the invention for the preparation of cosmetic, dermatological or pharmaceutical formulations. Consequently, the cosmetic, dermatological or pharmaceutical formulation comprising at least one emulsifier system according to the invention or at least one emulsion or dispersion according to the invention is likewise provided by the invention.

The cosmetic, dermatological or pharmaceutical formulations and also the care and cleansing compositions can, for example, comprise at least one additional component selected from the group of Emollients,
Emulsifiers and surfactants,
Thickeners/viscosity regulators/stabilizers,
UV photoprotective filters,
UV photoprotective particulate materials,
Antioxidants,
Hydrotropes
Polyols,
Solids and fillers,
Film formers,
Pearlescent additives,
Deodorant and antiperspirant active ingredients,
Insect repellents,
Self-tanning agents,
Preservatives,
Conditioners,
Perfumes,
Dyes,
Cosmetic active ingredients,
Care additives,
Superfatting agents,
Solvents.

Substances which can be used as exemplary representatives of the individual groups can be found in the German application DE 102008001788.4. This patent application is hereby incorporated by reference and thus forms part of the disclosure.

Emollients which can be used are all cosmetic oils, in particular mono- or diesters of linear and/or branched mono- and/or dicarboxylic acids having 2 to 44 carbon atoms with linear and/or branched saturated or unsaturated alcohols having 1 to 22 carbon atoms. The esterification products of aliphatic, difunctional alcohols having 2 to 36 carbon atoms with monofunctional aliphatic carboxylic acids having 1 to 22 carbon atoms can likewise be used. Also suitable are long-chain aryl acid esters, such as, for example, esters of benzoic acid, e.g. benzoic acid esters of linear or branched, saturated or unsaturated alcohols having 1 to 22 carbon atoms, or else isostearyl benzoate or octyldodecyl benzoate or for example $C_{12-15}$-alkyl benzoate, or esters of benzoic acid with linear or branched $C_6$-$C_{22}$-alcohols. Further monoesters suitable as emollients and oil components are, for example, the methyl esters and isopropyl esters of fatty acids having 12 to 22 carbon atoms, such as, for example, methyl laurate, methyl stearate, methyl oleate, methyl erucate, isopropyl palmitate, isopropyl myristate, isopropyl stearate, isopropyl oleate. Other suitable monoesters are, for example, n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, and also esters which are obtainable from technical-grade aliphatic alcohol cuts and technical-grade, aliphatic carboxylic acid mixtures, e.g. esters of unsaturated fatty alcohols having 12 to 22 carbon atoms and saturated and unsaturated fatty acids having 12 to 22 carbon atoms, as they are accessible from animal and vegetable fats. Also suitable are naturally occurring monoester and/or wax ester mixtures as they are present, for example, in jojoba oil or in sperm oil. Suitable dicarboxylic acid esters are, for example, di-n-butyl adipate, di-n-butyl sebacate, di(2-ethylhexyl)adipate, di(2-hexyldecyl)succinate, diisotridecyl azelate. Suitable diol esters are, for example, ethylene glycol dioleate, ethylene glycol diisotridecanoate, propylene glycol di(2-ethylhexanoate), butanediol diisostearate, butanediol dicaprylate/caprate and neopentyl glycol dicaprylate. Further emollients which can be used are carbonates as for example dicaprylyl carbonate or diethylhexyl carbonate. Emollients and oil components which can likewise be used are relatively long-chain triglycerides, i.e. triple esters of glycerol with three acid molecules, of which at least one is relatively long-chain. Mention may be made here, by way of example, of fatty acid triglycerides; as such, it is possible to use, for example, natural, vegetable oils, e.g. olive oil, sunflower oil, soybean oil, peanut oil, rapeseed oil, almond oil, sesame oil, avocado oil, castor oil, cocoa butter, palm oil, but also the liquid fractions of coconut oil or of palm kernel oil, and also animal oils, such as, for example, shark liver oil, cod liver oil, whale oil, beef tallow and butter fat. Moreover waxes such as beeswax, carnauba palm wax, spermaceti, lanolin and claw oil, the liquid fractions of beef tallow and also synthetic triglycerides of caprylic/capric acid mixtures, triglycerides of technical-grade oleic acid, triglycerides with isostearic acid, or from palmitic acid/oleic acid mixtures may be used as emollients and oil components. Furthermore, hydrocarbons, in particular also liquid paraffins and isoparaffins, can be used. Examples of hydrocarbons which can be used are paraffin oil, isohexadecane, polydecene, vaseline, paraffinum perliquidum, squalane, ceresine. Furthermore, it is also possible to use linear or branched fatty alcohols such as oleyl alcohol or octyldodecanol, and also fatty alcohol ethers such as dicaprylyl ether. Suitable silicone oils and silicone waxes are, for example, polydimethylsiloxanes, cyclomethylsiloxanes, and also aryl- or alkyl- or alkoxy-substituted polymethylsiloxanes or cyclomethylsiloxanes. Suitable further oil bodies are, for example, Guerbet alcohols based on fatty alcohols having 6 to 18, preferably 8 to 10, carbon atoms, esters of linear $C_6$-$C_{22}$-fatty acids with linear $C_6$-$C_{22}$-fatty alcohols, esters of branched $C_6$-$C_{13}$-carboxylic acids with linear $C_6$-$C_{22}$-fatty alcohols, esters of linear $C_6$-$C_{22}$-fatty acids with branched $C_8$-$C_{18}$-alcohols, in particular 2-ethylhexanol or isononanol, esters of branched $C_6$-$C_{13}$-carboxylic acids with branched alcohols, in particular 2-ethylhexanol or isononanol, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on C6-C18-fatty acids, esters of $C_6$-$C_{22}$-fatty alcohols and/or Guerbet alcohols with aromatic carboxylic acids, in particular benzoic acid, vegetable oils, branched primary alcohols, substituted cyclohexanes, linear $C_6$-$C_{22}$-fatty alcohol carbonates, Guerbet carbonates, dialkyl ethers, ring-opening products of epoxidized fatty acid esters with polyols.

UV photoprotective filters which can be used are, for example, organic substances which are able to absorb ultraviolet rays and release the absorbed energy again in the form of longer-wave radiation, e.g. heat. UVB filters may be oil-soluble or water-soluble. Oil-soluble UVB photoprotective filters to be mentioned are, for example: 3-benzylidenecamphor and derivatives thereof, e.g. 3-(4-methylbenzylidene) camphor, 4-aminobenzoic acid derivatives, such as, for example, 2-ethylhexyl 4-(dimethylamino)benzoate and amyl 4-(dimethylamino)benzoate, esters of cinnamic acid, such as, for example, 2-ethylhexyl 4-methoxycinnamate, isopentyl 4-methoxycinnamate, 2-ethylhexyl 2-cyano-3-phenylcinnamate (octocrylene), esters of salicylic acid, such as, for example, 2-ethylhexyl salicylate, 4-isopropylbenzyl salicylate, homomenthyl salicylate, derivatives of benzophenone, such as, for example, 2-hydroxy-4-methoxybenzophenone, 2-hydroxy-4-methoxy-4'-methylbenzophenone, 2,2'-dihydroxy-4-methoxybenzophenone, esters of benzalmalonic acid, such as, for example, di-2-ethylhexyl 4-methoxybenzmalonate, triazine derivatives, such as, for example, 2,4,6-trianilino-(p-carbo-2'-ethyl-1'-hexyloxy)-1,3,5-triazine and octyltriazone, propane-1,3-diones, such as, for example, 1-(4-tert-butylphenyl)-3-(4'-methoxyphenyl)propane-1,3-dione.

Suitable water-soluble UVB photoprotective filters are: 2-phenylbenzimidazole-5-sulphonic acid and alkali metal, alkaline earth metal, ammonium, alkylammonium, alkanolammonium and glucammonium salts thereof, sulphonic acid derivatives of benzophenone, such as, for example, 2-hydroxy-4-methoxybenzophenone-5-sulphonic acid and its salts, sulphonic acid derivatives of 3-benzylidenecamphor, such as, for example, 4-(2-oxo-3-bornylidenemethyl)benzenesulphonic acid and 2-methyl-5-(2-oxo-3-bornylidene)sulphonic acid and salts thereof.

Suitable typical UVA photoprotective filters are, in particular, derivatives of benzoylmethane, such as, for example, 1-(4'-tert-butylphenyl)-3-(4'-methoxyphenyl)propane-1,3-dione or 1-phenyl-3-(4'-isopropylphenyl)propane-1,3-dione. The UV-A and UV-B filters can of course also be used in mixtures.

Besides the specified soluble substances, insoluble pigments are also suitable for this purpose, namely finely disperse metal oxides or salts, such as, for example, titanium dioxide, zinc oxide, iron oxide, aluminium oxide, cerium oxide, zirconium oxide, silicates (talc), barium sulphate and zinc stearate. The particles here should have an average diameter of less than 100 nm, e.g. between 5 and 50 nm and in particular between 15 and 30 nm. They may have a spherical shape, although it is also possible to use those particles which have an ellipsoidal shape or a shape which deviates in some other way from the spherical form. A relatively new class of photoprotective filters are micronized organic pigments, such as, for example, 2,2'-methylenebis{6-(2H-benzotriazol-2-yl)-4-(1,1,3,3-tetramethylbutyl)phenol} with a particle size of <200 nm, which is obtainable, for example, as 50% strength aqueous dispersion.

Further suitable UV photoprotective filters can be found in the overview by P. Finkel in SÖFW-Journal 122, 543 (1996). Besides the two aforementioned groups of primary UV photoprotective filters, it is also possible to use secondary photoprotective agents of the antioxidant type which interrupt the photochemical reaction chain which is triggered when UV radiation penetrates into the skin. Antioxidants which can be used are, for example, superoxide dismutase, tocopherols (vitamin E), dibutylhydroxytoluene and ascorbic acid (Vitamin C).

In one preferred embodiment, the cosmetic, dermatological or pharmaceutical formulations according to the invention comprise as additional component particles or pigments, preferably those selected from the group titanium dioxide, zinc oxide, iron oxide, aluminium oxide, zirconium oxide, silicates (talc), and zinc stearate, nylon-12, boron nitride, polyacrylate or polymethyl acrylate particles or silicone elastomers.

In a likewise preferred embodiment, the cosmetic, dermatological or pharmaceutical formulations according to the invention comprise as additional component cosmetic or biogenic active ingredients, preferably those selected from the group: phytosphingosine (and phytosphingosin derivatives), sphingosine (and sphingosine derivatives), sphingolipids, tocopherol, tocopherol acetate, tocopherol palmitate, ascorbic acid, polyphenols, deoxyribonucleic acid, coenzyme Q10, retinol, AHA acids, amino acids, hyaluronic acid, alpha-hydroxy acids, flavones, isoflavones, stilbenes, catechines, polyglutamic acid, creatine (and creatine derivatives), guanidine (and guanidine derivatives), pseudoceramides, essential oils and fatty acids, peptides, preferably peptides comprising from 2 to 10 amino acids, oligopeptides, protein hydrolysates, plant extracts, bisabolol, allantoin, panthenol, phytantriol, idebenone, liquorice extract, plant extracts, glycyrrhizidine and idebenone, scleroglucan, β-glucan, santalbic acid and vitamin complexes.

Examples of plant extracts are horsechestnut extract, camomile extract, rosemary extract, black and red currant extract, birch extract, rosehip extract, licorice extract, algae extract, green tea extract, aloe extract, ginger extract, ginseng extract, ginkgo extract, grapefruit extract, calendula extract, camphor, curcuma extract, thyme extract, mangosteen extract, aloe extract, cystus extract, terminalia arjuna extract, oat extract, oregano extract, raspberry extract, strawberry extract, etc.

The biogenic active ingredients can also include the so-called barrier lipids, examples of which being ceramides, phytosphingosine and derivatives, sphingosine and derivatives, sphinganine and derivatives, pseudoceramides, phospholipids, lysophospholipids, cholesterol and derivatives, cholesteryl ester, free fatty acids, lanolin and derivatives, squalane, squalene and related substances.

Within the context of the invention, the biogenic active ingredients also include anti-acne, such as, for example, benzyl peroxide, phytosphingosine and derivatives, niacinamide hydroxybenzoate, nicotinaldehyde, retinol acid and derivatives, salicylic acid and derivatives, citronellic acid etc., and anti-cellulite, such as, for example, xanthine compounds such as caffeine, theophylline, theobromine and aminophylline, carnitine, carnosine, salicyloyl phytosphingosine, phytosphingosines, santalbic acid etc., as well as antidandruff agents such as, for example, salicylic acid and derivatives, zinc pyrithione, selenium sulphide, sulphur, cyclopiroxolamine, bifonazole, climbazole, octopirox and actirox etc., as well as astringents, such as, for example, alcohol, aluminium derivatives, gallic acid, pyridoxine salicylate, zinc salts, such as, for example, zinc sulphate, acetate, chloride, lactate, zirconium chlorohydrates etc. Bleaches such as kojic acid, arbutin, vitamin C and derivatives, hydroquinone, turmeric oil, creatinine, sphingolipids, oxyresveratrol, niacinamide, etc. may likewise be included in the biogenic active ingredients.

The dermatological or pharmaceutical formulations according to the invention may comprise alone or in combination with one or more of the actives mentioned above actives for antiperspirant or deodorant applications, as for example antiperspirants, esterase inhibitors, bactericidal or bacteriostatic agents, perspiration-absorbing substances and/or perfumes. Examples of those actives are given for example in US 2003053970.

Possible application forms of the emulsions and dispersions comprising the emulsifier system according to the invention are therefore sprays, lotions, creams, ointments and thus use over a very wide consistency range from water-thin to heavily pasty, in the extreme case even solid.

The emulsifier systems can therefore be used, for example, in care creams and lotions for face, body and hands, in sunscreen emulsions, in make-up, in aerosols, roll-ons, pump sprays, sticks e.g. in the antiperspirant/deodorant sector, in baby care products, in intimate care products, foot care products, hair care products, nail care products, dental care products or oral care products, and also in dermatological ointments.

In the examples given below, the present invention is described by way of example without any intention to limit the invention, the scope of application of which arises from the entire description and the claims, to the embodiments given in the examples.

The conversion (SiH value) is determined via the gas-volumetric SiH determination method (decomposition of SiH functions with sodium butanolate).

The invention is further described by the following non-limiting examples which further illustrate the invention, and are not intended, nor should they be interpreted to, limit the scope of the invention.

EXAMPLES

The viscosities given in the examples listed below were determined in a falling-ball viscometer in accordance with DIN 53015.

To determine the molecular weight ratios, the GPC method described above was used. The GPC data were acquired on a Hewlett Packard HP 1100 instrument with HP RI detector and the aforementioned parameters.

The compounds with the trade names starting with ABIL®, TEGO® and TEGOSOFT® mentioned in the examples are all available from Evonik Goldschmidt GmbH.

Example 1

Preparation of an Alkylsiloxane-Polyethersiloxane Copolymer in Accordance with Example 5 from EP-B-1 520 870

Example 1a

Hydrosilylation

In a multineck flask rendered inert with argon and equipped with precision-ground glass stirrer, dropping funnel and reflux condenser, 1675 g of a siloxane carrying pendant SiH groups and of the average composition MD75(DH)25M (SiH content: 3.6 mol/kg) were admixed at 21° C. with 5.025 ml of the catalyst solution described in EP-B-1 520 870 (12 wppm Pt).

Over the course of 40 minutes, 586.7 g of 1-hexadecene were added dropwise such that the heat of reaction increased the starting temperature to 66° C. Over the course of 30 minutes, 993.6 g of a polyether of average composition $CH_2=CH-CH_2O-(C_2H_4O)_8-H$ (iodine number: 62 g iodine/100 g) were then quickly added dropwise, during which the reaction temperature was kept at a maximum of 56° C. When the addition was complete, a further 304.8 g of 1-hexadecene were added over the course of 20 minutes. In contrast to Example 5 from EP-B-1 520 870, the mixture was immediately cooled to 20° C. after the metered addition. By immediately cooling directly after the metered addition, the conversion was 92.7% (SiH value: 0.12). The viscosity was 1165 mPas and the ratio of Mw/Mn was 10.2 (Table 1).

Example 1b

HV Processing (High-Viscosity Processing)

The product from the above reaction (1.8 kg) was heated to 110° C., admixed with 125 ppm of trispentafluorophenylborane (dissolved in allyl polyether solution) and stirred for 1 h. The resulting reaction product was then diluted (1:1) with the starting material (product from the above reaction) and cooled. Following the addition of 50 ppm of triisopropanolamine, the mixture was stirred for a further 30 min and then the high-viscosity product was drawn off. The viscosity was 3636 mPas and the ratio of Mw/Mn was 64.18 (Table 2).

Examples 2-14

Preparation of Hydrocarbon-Substituted Siloxane-Polyethersiloxane Copolymers

Examples 2a-14a

Hydrosilylation

The hydrosilylation was carried out in accordance with Example 1a. In contrast to Example 1a, the compounds listed in Table 1 were used. Moreover, after the hydrosilylation, a deodorization (hydration) as described in DE 10 2007 012 241 (U.S. Patent Appl. Pub. 2008-227923) was carried out.

For this, at a temperature of <90° C., 2.2 g of palladium on carbon, 1.6 g of Tonsil® (Slid-Chemie AG) and 22 g of water were added to 3.5 kg of an alkylsiloxane-polyethersiloxane copolymer according to Examples 2-14. The mixture was then heated to 120° C. and ca. 6 l of hydrogen was introduced per hour via a submerged tube, during which the operating pressure was atmospheric pressure. Altogether, hydrogen was passed through the mixture with vigorous stirring for 3 hours. Nitrogen (6 l/h) was then introduced via a submerged tube for 15 minutes. The reaction mixture was then freed from all volatile constituents at 5 mbar and 140° C. for 1 hour with the introduction of nitrogen (ca. 2 l/h).

After the deodorization, 2% by weight of triglycerol-4 isostearate were added to the resulting product. After cooling the sample, 0.2% by weight of filter aid (Harborlite 900/from Lehmann and Voss) was added and the sample was then filtered over deep-bed filter plates (HS1600 from Seitz-Schenk). The filtrate was then passed to the HV processing (high-viscosity processing). The viscosity and the Mw/Mn ratio of the deodorized products can be found in Table 1.

Examples 2b-14b

HV Processing (High-Viscosity Processing)

In each case 1.8 kg of the products from Examples 2-14 were heated to 110° C., admixed with the compound/compounds indicated in Table 2 as catalysts (dissolved in allyl polyether solution) and in the amount given in Table 2 (based on the present material to be condensed), and the reaction mixture was stirred at 110° C. for the reaction time given in Table 2. The resulting reaction product was then diluted with the starting material (products from the respective Examples 2a-14a) (mass ratio 1:1) and cooled. After adding 50 ppm of triisopropanolamine, the mixture was stirred for a further 30 min, and the high-viscosity product was drawn off.

The high-viscosity, clear modified siloxanes prepared in this way were characterized by means of the viscosity and the Mw/Mn ratio. The results can be found in Table 2.

TABLE 1

Use amounts and results for Examples 1a to 14a

| Ex. | Siloxanes | AK | U | Olefin | Polyether | EK | V | M |
|---|---|---|---|---|---|---|---|---|
| 1a | MD75(DH)25M | 3.6 | 92.7 | 1-Hexadecene | $CH_2=CH-CH_2O-(C_2H_4O)_8-H$ (Iodine number: 62) | 0.12 | 1165 | 10.2 |
| 2a | MD75(DH)25M | 3.6 | ~94 | 1-Hexadecene | $CH_2=CH-CH_2O-(C_2H_4O)_8-H$ (Iodine number: 62) | ~0.16 | 1051 | 10.58 |
| 3a | MD75(DH)25M | 3.6 | ~94 | 1-Hexadecene | $CH_2=CH-CH_2O-(C_2H_4O)_8-H$ (Iodine number: 62) | ~0.06 | 1051 | 10.58 |
| 4a | MD75(DH)25M | 3.6 | ~94 | 1-Hexadecene | $CH_2=CH-CH_2O-(C_2H_4O)_8-H$ (Iodine number: 62) | ~0.06 | 1098 | 10.84 |
| 5[a] | MD75(DH)25M | 3.6 | ~94 | 1-Hexadecene | $CH_2=CH-CH_2O-(C_2H_4O)_8-H$ (Iodine number: 62) | ~0.12 | 1096 | 10.77 |
| 6[a] | MD75(DH)25M | 3.6 | ~94 | 1-Hexadecene | $CH_2=CH-CH_2O-(C_2H_4O)_8-H$ (Iodine number: 62) | ~0.1 | 1042 | 10.64 |
| 7[a] | MD75(DH)25M | 3.6 | ~94 | 1-Hexadecene | $CH_2=CH-CH_2O-(C_2H_4O)_8-H$ (Iodine number: 62) | ~0.1 | 1105 | 10.9 |

TABLE 1-continued

Use amounts and results for Examples 1a to 14a

| Ex. | Siloxanes | AK | U | Olefin | Polyether | EK | V | M |
|---|---|---|---|---|---|---|---|---|
| 8a | MD75(DH)25M | 3.6 | 94.2 | 1-Dodecene | $CH_2=CH-CH_2O-(C_2H_4O)_8-H$ (Iodine number: 62) | 0.12 | 1157 | 8.12 |
| 9a | MD75(DH)25M | 3.6 | 92.1 | α-Olefin C20-24 | $CH_2=CH-CH_2O-(C_2H_4O)_8-H$ (Iodine number: 62) | | Solid at RT | 11.77 |
| 10a | MD75(DH)25M | 3.6 | 93.0 | 1-Hexadecene | $CH_2=CH-CH_2O-(C_2H_4O)_{9.5}-(C_3H_6O)_2-H$ (Iodine number: 42) | | 1608 | 9.20 |
| 11a | MD75(DH)25M | 3.6 | 95.6 | 1-Hexadecene | $CH_2=CH-CH_2O-(C_2H_4O)_{13}-(C_3H_6O)_{3.5}-H$ (Iodine number: 30) | | 4141 | 10.59 |
| 12a | MD75(DH)25M | 3.6 | 85.2 | α-Methylstyrene | $CH_2=CH-CH_2O-(C_2H_4O)_8-H$ (Iodine number: 62) | | 1622 | 10.82 |
| 13a | MHD123(DH)25MH | 2.5 | 92.0 | 1-Hexadecene | $CH_2=CH-CH_2O-(C_2H_4O)_8-H$ (Iodine number: 63) | | 1784 | 15.80 |
| 14a | MED55(DH)8MH | 2.1 | 93.3 | 1-Hexadecene | $CH_2=CH-CH_2O-(C_2H_4O)_8-H$ (Iodine number: 63) | | 323 | 5.73 |

AK: Si—H Concentration before the start of the reaction (moles/kg)
EK: Si—H Concentration after the end of the reaction (moles/kg)
U: Si—H Conversion (% moles)
M: Mw/Mn ratio
V: Viscosity (mPas)
α-Olefin C20-24: Product from Chevron Phillips

TABLE 2

Results for examples 1b to 14b

| Ex. | Catalyst | KK | RZ | V | M |
|---|---|---|---|---|---|
| 1b | Trispentafluorotriphenylborane | 125 | 1 | 3636 | 64.18 |
| 2b | Trispentafluorotriphenylborane | 125 | 2 | 3658 | 60.98 |
| 3b | Trispentafluorotriphenylborane | 200 | 10 | 6066 | 118.77 |
| 4b | Trispentafluorotriphenylborane | 125 | 1 | 3683 | 65.25 |
| 5b | Sc(OTf)$_3$ × Hydrate Trispentafluorotriphenylborane | 287 125 | 12 | 1908 | 23.54 |
| 6b | Sc(OTf)$_3$ × Hydrate | 281 | 6 | 1580 | 20.54 |
| 7b | Tetra n-propoxytitanate Tetraethoxysilane | 300 2200 | 8 | 1493 | 15.18 |
| 8b | Trispentafluorotriphenylborane | 200 | 6 | 2681 | 23.96 |
| 9b | Trispentafluorotriphenylborane | 200 | 7 | Solid at RT | 25.87 |
| 10b | Trispentafluorotriphenylborane | 325 | 10 | 1885 | 12.54 |
| 11b | Trispentafluorotriphenylborane | 325 | 11 | 5650 | 18.08 |
| 12b | Trispentafluorotriphenylborane | 325 | 7 | 2594 | 17.98 |
| 13b | Trispentafluorotriphenylborane | 200 | 4 | 2843 | 26.91 |
| 14b | Trispentafluorotriphenylborane | 325 | 15 | 630 | 15.71 |

KK: Catalyst concentration (wppm)
M: Mw/Mn ratio
RZ: Reaction time (h)
V: Viscosity (mPas)

TABLE 3

Composition of the formulations of example 15

| INGREDIENTS | % w/w |
|---|---|
| Emulsifier | 2.5 |
| Cyclopentasiloxane | 20.00 |
| Caprylic/Capric Triglyceride (TEGOSOFT ® CT) | 5.00 |
| Ethylhexyl Palmitate (TEGOSOFT ® OP) | 5.00 |
| Titanium Dioxide; Trimethoxycaprylylsilane (TEGO Sun T 805) | 6.40 |
| Iron oxide US Cosmetics Corp. | 1.90 |
| Talc J-68-SAT (silicone treated talc) | 1.60 |
| Water | 54.50 |
| NaCl | 0.80 |
| Propylene glycol | 2.00 |
| Propylene Glycol; Diazolidinyl Urea; Methylparaben; Propylparaben (Germaben II) | 0.30 |

Example 15

Experiments on the Long-Term Stability of High Cyclic Siloxane Emulsion

As a basic system emulsions were prepared according to the formulation in Table 3. Inventive emulsifiers were compared with the commercially available state-of-the-art emulsifiers Cetyl PEG/PPG 10/1 Dimethicone (ABIL® EM 90, Evonik Goldschmidt GmbH) and Lauryl PEG/PPG-18/18 Methicone (Dow Corning 5200 Formulation Aid).

The preparation of the emulsions was carried out in the following manner:

A portion of the oil phase was blended using emulsifier, Caprylic/Capric Triglyceride (TEGOSOFT® CT from Evonik Goldschmidt GmbH), Ethylhexyl Palmitate (TEGOSOFT® OP from Evonik Goldschmidt GmbH), and Titanium Dioxide; Trimethoxycaprylylsilane (TEGO® Sun T 805 from Evonik Goldschmidt GmbH). This mixture was then passed three times through a 3 roller mill. The final particle size was measured using a Hegman gauge and determined to be approximately 7 microns.

The remaining components of the oil phase (cyclopentasiloxane, talc and iron oxides) were added to the pre-milled mixture. Once these additions were complete the mixture was allowed to blend until homogeneous.

The aqueous phase (water, sodium chloride, propylene glycol and propylene glycol; diazolidinyl urea; methylparaben; propylparaben) was dispensed at a controlled rate (~1 hour) using a separatory funnel. Thorough, but not too intense agitation was used to ensure complete incorporation into the oil phase. Homogenization was conducted for 5 minutes at a rate of ~1500 rpm using a Caframo overhead mixer.

The emulsions were stored at room temperature (25° C.), 40° C., 45° C. and 50° C. and the condition was monitored at weekly intervals. Emulsions in which phase separation or demixing was evident were denoted with −, emulsions which were faultless were denoted with +. Emulsifiers with the emulsifier system according to the invention were referred to as example number 1b from table 2 as E, those with ABIL® EM 90 as A and those with Dow Corning DC 5200 Formulation Aid as D. The results are given in Table 4.

TABLE 4

Results of example 15

| Emulsifier | Temp. | 1 Week | 2 Weeks | 3 Weeks | 5 Weeks | 2 Months | 3 Months | 6 Months |
|---|---|---|---|---|---|---|---|---|
| A | RT | + | + | − | − | − | − | − |
| A | 40 | + | − | − | − | − | − | − |
| A | 45 | + | − | − | − | − | − | NA |
| A | 50 | − | − | − | − | NA | NA | NA |
| E | RT | + | + | + | + | + | + | + |
| E | 40 | + | + | + | + | + | + | + |
| E | 45 | + | + | + | + | + | + | NA |
| E | 50 | + | + | + | + | NA | NA | NA |
| D | RT | + | + | + | − | − | − | − |
| D | 40 | − | − | − | − | − | − | − |
| D | 45 | − | − | − | − | − | − | NA |
| D | 50 | − | − | − | − | NA | NA | NA |

+ = stable
− = unstable

NA = not applicable

As can clearly be seen from Table 4, the emulsifier system according to the invention displays clear advantages with regard to the long-term stability compared to conventional emulsifier systems.

Example 16

Experiments on the High Temperature Stability

Utilizing silicone emulsifier structure 1b from Table 2 was tested at 70° C. and was stable for 2+ months:

TABLE 5

Composition of the formulation of example 16

| INGREDIENTS | % w/w | % w/w |
|---|---|---|
| Emulsifier ex. 1b (Table 2) inventive | 2.00 | |
| Lauryl PEG/PPG-18/18 Methicone (Dow Corning DC 5200) | | 2.00 |
| Mineral Oil | 6.00 | 6.00 |
| Ethylhexyl Palmitate (TEGOSOFT ® OP) | 6.00 | 6.00 |
| Caprylic/Capric Triglyceride (TEGOSOFT ® CT) | 6.00 | 6.00 |
| Hydrogenated Castor Oil | 0.80 | 0.80 |
| Bees Wax | 1.20 | 1.20 |
| Water | 76.70 | 76.70 |

TABLE 5-continued

Composition of the formulation of example 16

| INGREDIENTS | % w/w | % w/w |
|---|---|---|
| Sodium Chloride | 1.00 | 1.00 |
| Propylene Glycol; Diazolidinyl Urea; Methylparaben; Propylparaben (Germaben II) | 0.30 | 0.30 |
| Results | stable | Not stable |

The present invention showed unexpected stability at elevated temperatures against Lauryl PEG/PPG-18/18 Methicone. The present invention was tested for 2 months and showed no signs of emulsion failure whereas the system with the state-of-the-art emulsifier was not stable and separated within 24 hours.

Example 17

Quick Break Emulsion

TABLE 6

Composition of the formulation of example 17

| INGREDIENTS | % w/w | % w/w | % w/w |
|---|---|---|---|
| Emulsifier ex. 1b (Table 2) | 0.80 | | |
| Emulsifier ex. Cetyl PEG/PPG 10/1 Dimethicone (ABIL ® EM 90) | | 0.80 | |
| Lauryl PEG/PPG-18/18 Methicone (Dow Corning DC 5200) | | | 0.80 |
| Cetyl Dimethicone (ABIL ® Wax 9801) | 1.60 | 1.60 | 1.60 |
| Diethylhexyl Carbonate (TEGOSOFT ® DEC) | 2.00 | 2.00 | 2.00 |
| Dimethicone (ABIL ® 350) | 1.00 | 1.00 | 1.00 |
| Cyclopentasiloxane | 4.00 | 4.00 | 4.00 |
| Water | 84.30 | 84.30 | 84.30 |
| Propylene Glycol | 5.00 | 5.00 | 5.00 |
| Sodium Chloride | 1.00 | 1.00 | 1.00 |

TABLE 6-continued

Composition of the formulation of example 17

| INGREDIENTS | % w/w | % w/w | % w/w |
|---|---|---|---|
| Propylene Glycol; Diazolidinyl Urea; Methylparaben; Propylparaben (Germaben II) | 0.30 | 0.30 | 0.30 |
| | Stable | Not Stable | Not Stable |

The present invention was able to be pneumatically pumped without emulsion instability. The state-of-the-art emulsified systems with ABIL EM 90 or Dow Corning DC 5200 Formulation Aid showed extreme separation upon being pumped.

Example 18

Sunscreen Lotion W/O Crystal Inhibiting Properties

TABLE 7

Composition of the formulation of example 18

| INGREDIENTS | % w/w | % w/w | % w/w |
|---|---|---|---|
| Emulsifier ex. 1b (Table 2) | 1.50 | | |
| Emulsifier ex. (Table 1) Cetyl PEG/PPG 10/1 Dimethicone (ABIL ® EM 90) | | 1.50 | |
| Lauryl PEG/PPG-18/18 Methicone state-of-the-art | | | 1.50 |
| Cetyl Dimethicone (ABIL ® Wax 9801) | 0.50 | 0.50 | 0.50 |
| C12-15 Alkyl Benzoate (TEGOSOFT ® TN 2) | 2.00 | 2.00 | 2.00 |
| Ethylhexyl Palmitate (TEGOSOFT ® OP) | 2.00 | 2.00 | 2.00 |
| Diethylhexyl Carbonate (TEGOSOFT ® DEC) | 2.00 | 2.00 | 2.00 |
| Octocrylene | 10.00 | 10.00 | 10.00 |
| Homosalate | 15.00 | 15.00 | 15.00 |
| Oxybenzone | 3.00 | 3.00 | 3.00 |
| Avobenzone | 3.00 | 3.00 | 3.00 |
| Microcrystalline Wax | 0.20 | 0.20 | 0.20 |
| Beeswax | 0.15 | 0.15 | 0.15 |
| Water | 59.85 | 59.85 | 59.85 |
| Sodium chloride | 0.80 | 0.80 | 0.80 |
| Propylene Glycol; Diazolidinyl Urea; Methylparaben; Propylparaben (Germaben II) | q.s. | q.s. | q.s. |
| Crystal formation after 1 month, 25° C. | no | yes | yes |

The inventive emulsifier was clearly able to inhibit crystal formation. This was observed under a microscope with an amplification of 40× and 100× at 1 month.

Example 19

Critical Formulation with Ethanol

TABLE 8

Composition of the formulation of example 19

| INGREDIENTS | % w/w | % w/w | % w/w | % w/w |
|---|---|---|---|---|
| Emulsifier ex. 1b (Table 2) | 1.20 | | | |
| Emulsifier ex. Cetyl PEG/PPG 10/1 Dimethicone (ABIL ® EM 90) | | 1.20 | | |
| Lauryl PEG/PPG-18/18 Methicone | | | 1.20 | |
| Dimethicone/Vinyl Dimethicone Crosspolyme (and) Cyclotetrasiloxane | | | | 1.20 |

TABLE 8-continued

Composition of the formulation of example 19

| INGREDIENTS | % w/w | % w/w | % w/w | % w/w |
|---|---|---|---|---|
| Ethylhexyl Palmitate (TEGOSOFT ® OP) | 11.90 | 11.90 | 11.90 | 11.90 |
| Caprylic/Capric Triglyceride (TEGOSOFT ® CT) | 11.90 | 11.90 | 11.90 | 11.90 |
| Sodium chloride | 0.80 | 0.80 | 0.80 | 0.80 |
| Glycerine | 3.00 | 3.00 | 3.00 | 3.00 |
| Water | 65.20 | 65.20 | 65.20 | 65.20 |
| Phenoxyethanol; Methylparaben; Propylparaben; Ethylparaben (Phenonip ® XB) | 1.00 | 1.00 | 1.00 | 1.00 |
| Ethanol | 5.00 | 5.00 | 5.00 | 5.00 |

The inventive emulsifier formed water droplets that were more compact and even in size than the state-of-the-art ABIL EM 90 and Dow Corning DC 5200 Formulation Aid. The mixture of dimethicone/vinlydimethicone crosspolymer and cyclotetrasiloxane (Shin Etsu KSG-17) was not able to form an emulsion.

Example 20-35

Some Formulations for Different Applications

The following examples show further capabilities with the inventive emulsifier without comparison:

TABLE 9

Overview of the formulations and the corresponding example number

| | |
|---|---|
| Powdery Feel Daily Wear lotion with UV Protection | Example 20 |
| Body Lotion with low polar oils | Example 21 |
| In combination with high polar oils | Example 22 |
| SKIN SOFTENING LOTION (W/O Emulsion - Cold Process) | Example 23 |
| W/O SHEER MAKE-UP | Example 24 |
| WATER-IN-OIL MASCARA | Example 25 |
| Barrier Cream | Example 26 |
| W/O AFTER SHAVE LOTION (Cold Process) | Example 27 |
| DIHYDROXYACETONE LOTION | Example 28 |
| Clear AHA Gel | Example 29 |
| Clear BHA Gel | Example 30 |
| Clear Sunscreen Gel | Example 31 |
| W/O ALCOHOL LOTIONS | Example 32 |
| DIAPER CREAM (W/O Emulsion) | Example 33 |
| GLOSSY LIPSTICK | Example 34 |
| Sunscreen with organic and inorganic filters | Example 35 |

Example 20

Formulation with Cationic Ingredient for a Powdery Skin Feel

TABLE 10

Composition of the formulation of example 20

| INGREDIENTS | % w/w |
|---|---|
| Emulsifier 6b | 1.50 |
| Cetearyl Alcohol; Palmitamidopropyltrimonium Chloride (Tego ® Care CE 40) | 1.00 |
| Cetyl Dimethicone (ABIL ® Wax 9801) | 1.50 |
| Stearyl Heptanoate (TEGOSOFT ® SH) | 2.00 |
| Diethylhexyl Carbonate (TEGOSOFT ® DEC) | 5.00 |

TABLE 10-continued

Composition of the formulation of example 20

| INGREDIENTS | % w/w |
| --- | --- |
| Dimethicone (ABIL ® 350) | 1.00 |
| C12-15 Alkyl Benzoate (TEGOSOFT ® TN2) | 3.00 |
| Ethylhexyl Methoxycinnamate | 7.50 |
| Microcrystalline Wax | 1.20 |
| Hydrogenated Castor Oil | 0.80 |
| Water | q.s. |
| Preservative | q.s. |
| Propylene Glycol | 2.00 |
| Sodium Chloride | 0.80 |
| | 100.00 |

Example 21

Formulation with Low Polar Oils

TABLE 11

Composition of the formulation of example 21

| Ingredients | % w/w |
| --- | --- |
| Emulsifier 13b | 2.00 |
| Cyclopentasiloxane | 5.00 |
| Mineral Oil | 5.00 |
| Caprylic/Capric Triglyceride (TEGOSOFT ® CT) | 5.00 |
| Ethylhexyl Stearate (TEGOSOFT ® OS) | 5.00 |
| Isopropyl Myristate (TEGOSOFT ® M) | 5.00 |
| Water | 72.20 |
| Sodium Chloride | 0.80 |
| Preservative | q.s. |
| | 100.00 |

Example 22

Formulation with High Polar Oils

TABLE 12

Composition of the formulation of example 22

| Ingredients | % w/w |
| --- | --- |
| Emulsifier 1b | 2.00 |
| Cyclopentasiloxane | 5.00 |
| Mineral Oil | 5.00 |
| Caprylic/Capric Triglyceride (TEGOSOFT ® CT) | 5.00 |
| Ethylhexyl Stearate (TEGOSOFT ® OS) | 5.00 |
| Isopropyl Myristate (TEGOSOFT ® M) | 5.00 |
| Water | 72.20 |
| Sodium Chloride | 0.80 |
| Preservative | q.s. |
| | 100.00 |

Example 23

Cold Processable Formulation

TABLE 13

Composition of the formulation of example 23

| INGREDIENTS | % w/w |
| --- | --- |
| PHASE A | |
| Emulsifier 1b | 1.50 |
| Mineral Oil | 8.50 |
| Ethylhexyl Stearate (TEGOSOFT ® OS) | 6.00 |
| Cetearyl Ethylhexanoate (TEGOSOFT ® Liquid) | 7.00 |
| Cetyl Dimethicone (ABIL ® Wax 9814) | 1.00 |
| PHASE B | |
| Water | 75.00 |
| Distearyldimonium Chloride | 1.00 |
| Preservatives | q.s. |
| PHASE C | |
| Fragrance | q.s. |
| | 100.00 |

Example 24

Formulation for Color Cosmetic Application

TABLE 14

Composition of the formulation of example 24

| INGREDIENTS | % w/w |
| --- | --- |
| PHASE A | |
| Emulsifier 9b | 1.50 |
| Cetyl Dimethicone (ABIL ® Wax 9840) | 2.00 |
| Ethylhexyl Palmitate (TEGOSOFT ® OP) | 3.00 |
| Hydrogenated Castor Oil | 0.40 |
| Beeswax | 0.80 |
| Decyl Oleate (TEGOSOFT ® DO) | 1.50 |
| Dimethicone 350 cst | 0.25 |
| Ethylhexyl Stearate (TEGOSOFT ® OS) | 3.00 |
| PHASE B | |
| Cyclopentasiloxane | 15.75 |
| PHASE C | |
| Iron Oxides; Red, Yellow, Black, Brown | 0.30 |
| Titanium Dioxide; Trimethoxy-caprylylsilane (TEGO ® Sun T805G) | 2.10 |
| PHASE D | |
| Water | 66.90 |
| Sodium Chloride | 0.50 |
| Propylene Glycol | 2.00 |
| | 100.00 |

The formulation of this example was made following the procedure:
1. Combine ingredients of phase A and heat to 80° C.
2. Cool to 70° C. Add phase B.
3. Add ingredients of phase C. Mix with high shear.
4. Combine phase D and heat to 70° C. Add phase D to phase ABC.
5. Homogenize for a short period of time and transfer to over-head mixing.
6. Cool while mixing to <30° C. and homogenize.

Example 25

Color Cosmetics Mascara Formulation

TABLE 15

Composition of the formulation of example 25

| INGREDIENTS | % w/w |
| --- | --- |
| PHASE A | |
| Emulsifier 3b | 1.50 |
| Petrolatum | 4.00 |
| Petroleum Distillate | 10.00 |
| Beeswax | 2.50 |
| Hydrogenated Castor Oil | 2.50 |
| Ethylhexyl Palmitate (TEGOSOFT ® OP) | 5.00 |
| PHASE B | |
| Cyclopentasiloxane | 6.50 |
| PHASE C | |
| Propylene Glycol | 2.00 |
| Water | 59.70 |
| Sodium Chloride | 0.80 |
| Preservatives | q.s. |
| PHASE D | |
| Iron Oxides | 5.50 |
| Fragrance | q.s. |
| | 100.00 |

Example 26

Barrier Cream Formulation

TABLE 16

Composition of the formulation of example 26

| INGREDIENTS | % w/w |
| --- | --- |
| PHASE A | |
| Emulsifier 13b | 1.50 |
| Petrolatum | 4.50 |
| Ethylhexyl Stearate (TEGOSOFT ® OS) | 5.00 |
| Cetyl Dimethicone (ABIL ® Wax 9840) | 1.50 |
| Dimethicone | 3.00 |
| Mineral Oil | 4.00 |
| Hydrogenated Castor Oil | 0.80 |
| Beeswax | 1.20 |
| PHASE B | |
| Water | 77.60 |
| Sodium Chloride | 0.60 |
| Propylene Glycol (and) Diazolidinyl Urea (and) Methylparaben (and) Propylparaben | 0.30 |
| | 100.00 |

Example 27

After Shave Lotion

TABLE 17

Composition of the formulation of example 27

| INGREDIENTS | % w/w |
| --- | --- |
| PHASE A | |
| Emulsifier 1b | 1.50 |
| Cyclopentasiloxane | 20.00 |
| Tocopherol Acetate | 0.50 |
| Fragrance | q.s. |
| PHASE B | |
| Water | 75.40 |
| Sodium Chloride | 0.50 |
| Lactic Acid | 0.10 |
| Panthenol (50% ig) | 1.00 |
| Sodium Lactate; Sodium PCA; Glycine; Fructose; Urea; Niacinamide; Inositol; Sodium Benzoate; Lactic Acid | 1.00 |
| Preservatives | q.s. |
| | 100.0 |

Example 28

Self Tanner Formulation

TABLE 18

Composition of the formulation of example 28

| INGREDIENTS | % w/w |
| --- | --- |
| PHASE A | |
| Emulsifier 1b | 1.50 |
| Ethylhexyl Stearate | 4.00 |
| Isohexadecane | 7.00 |
| Hydrogenated Castor Oil | 0.40 |
| Beeswax | 0.40 |
| PHASE B | |
| Cyclopentasiloxane | 6.00 |
| PHASE C | |
| Water | 72.90 |
| Propylene Glycol | 2.00 |
| Sodium Chloride | 0.80 |
| Dihydroxyacetone | 5.00 |
| Preservatives | q.s. |
| Color | q.s. |
| PHASE D | |
| Fragrance | q.s. |
| | 100.0 |

Example 29

Gel Formulation

TABLE 19

Composition of the formulation of example 29

| INGREDIENTS | % w/w |
|---|---|
| Bis-Peg/PPG-14/14 Dimethicone (and) Cyclopentasiloxane (ABIL ® EM 97) | 3.00 |
| Emulsifier 13b | 1.00 |
| Cyclopentasiloxane (and) Dimethiconol (ABIL ® OSW5) | 1.00 |
| Isopropyl Myristate (TEGOSOFT ® M) | 3.00 |
| Cyclopentasiloxane | 14.00 |
| Phenyl Trimethicone | 1.00 |
| Bis-PEG/PPG-20/20 Dimethicone (ABIL ® B8832) | 0.25 |
| Fragrance | q.s. |
| Deionized Water | 20.25 |
| Magnesium Sulfate | 0.80 |
| Propylene Glycol | 50.10 |
| Lactic Acid (85%) | 1.00 |
| PEG-30 Glyceryl Laurate | 0.30 |
| SD Alcohol 40 | 4.30 |
| Preservative | q.s. |
| Sodium Hydroxide (10% aqueous solution) adjust pH to 4.0-4.5 | q.s. |
| | 100.00 |

Example 30

Gel Formulation

TABLE 20

Composition of the formulation of example 30

| INGREDIENTS | % w/w |
|---|---|
| Bis-PEG/PPG-14/14 Dimethicone (and) Cyclopentasiloxane (ABIL ® EM 97) | 3.00 |
| Emulsifier 3b | 1.00 |
| Cyclopentasiloxane (and) Dimethiconol (ABIL ® OSW5) | 1.00 |
| Bis-PEG/PPG-20/20 Dimethicone (ABIL ® B 8832) | 0.50 |
| Isopropyl Myristate (TEGOSOFT ® M) | 3.00 |
| Cyclopentasiloxane | 14.00 |
| Phenyl Trimethicone | 1.00 |
| Fragrance | q.s. |
| Deionized Water | 19.00 |
| Magnesium Sulfate | 1.20 |
| Propylene Glycol | 51.00 |
| Salicylic Acid USP | 1.00 |
| PEG-30 Glyceryl Laurate | 0.30 |
| Preservative | q.s. |
| SD Alcohol 40 | 4.00 |
| Sodium Hydroxide (10% Aqueous Solution) Adjust pH to 3.5-4.0 | q.s. |
| | 100.00 |

Example 31

Gel Formulation

TABLE 21

Composition of the formulation of example 31

| INGREDIENTS | % w/w |
|---|---|
| PHASE A | |
| Bis - PEG/PPG - 14/14 Dimethicone (and) Cyclopentasiloxane (ABIL ® EM 97) | 2.00 |
| Emulsifier 1b | 1.50 |
| Cyclopentasiloxane | 13.00 |
| Ethylhexyl Palmitate (TEGOSOFT ® OP) | 1.50 |
| Cetyl Dimethicone (ABIL ® Wax 9801) | 1.00 |
| Ethylhexyl Methoxycinnamate | 3.00 |
| Ethylhexyl Salicylate | 3.00 |
| Fragrance | q.s. |
| PHASE B | |
| Deionized Water | 18.00 |
| Propylene Glycol | 27.50 |
| Magnesium Sulfate | 2.50 |
| Glycerin USP | 26.00 |
| SD Alcohol 40 | 1.00 |
| Preservative | q.s. |
| | 100.00 |

Example 32

Lotion with Alcohol

TABLE 22

Composition of the formulation of example 32

| INGREDIENTS | % w/w |
|---|---|
| PHASE A | |
| Emulsifier 1b | 1.50 |
| Mineral Oil | 16.00 |
| Ethylhexyl Stearate | 1.50 |
| Cetyl Dimethicone (ABIL ® Wax 9801) | 1.50 |
| Hydrogenated Castor Oil | 0.50 |
| Synthetic Wax | 0.50 |
| PHASE B | |
| Cyclopentasiloxane | 5.50 |
| PHASE C | |
| Water | 62.30 |
| Sodium Chloride | 0.50 |
| Carbomer 940 (1.5% - NaOH Neutralized) | 0.20 |
| SD Alcohol 40A | 10.00 |
| PHASE D | |
| Fragrance, Preservatives | q.s. |
| | 100.00 |

Example 33

Barrier Cream for skin Protection

TABLE 23

Composition of the formulation of example 33

| INGREDIENTS | % w/w |
|---|---|
| PHASE A | |
| Emulsifier 13b | 1.50 |
| Petrolatum | 4.50 |
| Dimethicone (500 cs) | 3.50 |
| Cetyl Dimethicone (ABIL ® Wax 9840) | 1.50 |
| Ethylhexyl Stearate (TEGOSOFT ® OS) | 5.50 |
| Mineral Oil | 4.00 |
| Hydrogenated Castor Oil | 0.80 |
| Synthetic Wax | 1.20 |
| PHASE B | |
| Water | 76.90 |
| Sodium Chloride | 0.60 |
| Preservatives | q.s. |
| PHASE C | |
| Fragrance | q.s. |
| | 100.00 |

Example 34

Color Cosmetics: Lipstick Formulation

TABLE 24

Composition of the formulation of example 34

| INGREDIENTS | % w/w |
|---|---|
| PHASE A | |
| Carnauba | 3.00 |
| Candelilla Wax | 8.00 |
| Ozokerite | 1.60 |
| Microcrystalline Wax | 2.00 |
| Ethylhexyl Palmitate (TEGOSOFT ® OP) | 7.00 |
| Cetyl Ethylhexanoate (TEGOSOFT ® CO) | 5.00 |
| Lanolin Oil | 15.00 |
| Castor Oil USP | 22.50 |
| Emulsifier 1b | 0.75 |
| Stearoxy Dimethicone (ABIL ® Wax 2434) | 0.75 |
| PHASE B | |
| Castor Oil USP | 15.00 |
| Iron Oxides | 1.40 |
| D & C Red No. 6 Ba Lake | 1.75 |
| D & C Red No. 7 Ca Lake | 1.25 |
| PHASE C | |
| Bismuth Oxychloride | 15.00 |
| Antioxidants | q.s. |
| | 100.00 |

Example 35

Sunscreen Formulation

TABLE 25

Composition of the formulation of example 35

| INGREDIENTS | % w/w |
|---|---|
| PHASE A | |
| Emulsifier 1b | 2.00 |
| Ethylhexyl Stearate (TEGOSOFT ® OS) | 12.00 |
| Cyclopentasiloxane | 8.00 |
| Cetyl Dimethicone (ABIL ® Wax 9801) | 3.00 |
| Hydrogenated Castor Oil | 0.50 |
| Microcrystalline Wax | 1.00 |
| Mineral Oil | 2.00 |
| PHASE B | |
| Titanium Dioxide; Trimethoxy-caprylylsilane (TEGO ® Sun T805G)) | 8.00 |
| PHASE C | |
| Water | 63.00 |
| Sodium Chloride | 0.50 |
| PHASE D | |
| Fragrance, Preservatives | q.s. |
| | 100.00 |

Having thus described in detail various embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A crosslinked organopolysiloxane comprising:
organopolysiloxane units; and
building blocks which link the organopolysiloxane units;
wherein the building blocks are identical or different blocks of the formula (I):

$$-CH_2-CH_2-(G)_nO(EO)_x(PO)_y(XO)_z- \quad (I);$$

where G=divalent organic radical;
where $EO=(C_2H_4O)$
where $PO=(C_3H_6O)$
where $XO=(C_2H_3R^5O)$
where n=1 to 16;
where x=2 to 50;
where y=0 to 50;
where z=0 to 10; and
where $R^5$=independently of one another, identical or different radicals selected from the group consisting of:
alkyl radicals having 2 to 16 carbon atoms, which are optionally interrupted by ether functions;
alkaryl radicals having 7 to 18 carbon atoms; and
aryl radicals having 6 to 16 carbon atoms; and
where the building blocks of the formula (I) are directly linked to an Si atom at both linkage points, so that there is an SiC bond at one linkage point and a COSi bond at the other linkage point.

2. The crosslinked organopolysiloxane according to claim 1;
wherein the organopolysiloxane units are identical or different units of the formula (II):

$$M_{2+c+2d}D_aD'_bT_cQ_d \quad (II);$$

where $M=(R^1R^2{}_2SiO_{1/2})$;
where $D=(R^2{}_2SiO_{2/2})$;
where $D'=(R^2R^3SiO_{2/2})$;
where $T=(R^2SiO_{3/2})$;
where $Q=(SiO_{4/2})$;
where a=30 to 800;
where b=1 to 40;
where c=0 to 2;
where d=0 to 2;
where $R^1=R^2$ or $R^3$;
where $R^2$=independently of one another, V or H, or identical or different linear or branched, optionally aromatic, hydrocarbon radicals having 1 to 32 carbon atoms, which optionally carry OH or ester functions;
where $R^3$=independently of one another, identical or different polyether radicals of the general formula (III):

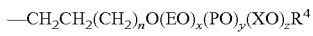 (III);

where $EO=(-C_2H_4O-)$;
where $PO=(-C_3H_6O-)$;
where $XO=(C_2H_3R^5O)$;
where n=1 to 16;
where x=2 to 50;
where y=0 to 50;
where z=0 to 10;
where $R^4$=independently of one another, identical or different radicals selected from the group consisting of H, alkyl radicals having 1 to 16 carbon atoms, and carboxylate radicals; and
where $R^5$=independently of one another, identical or different radicals selected from the group consisting of:
  alkyl radicals having 2 to 16 carbon atoms, which are optionally interrupted by ether functions;
  alkaryl radicals having 7-18 carbon atoms; and
  aryl radicals having 6 to 16 carbon atoms;
where V=a bond to the building block of the formula I; and
where at least one V is present per organopolysiloxane unit (II).

3. The crosslinked organopolysiloxane according to claim 2;
wherein, on average, at least one building block (I) is attached via an COSi bond per organopolysiloxane unit of the formula (II).

4. The crosslinked organopolysiloxane according to claim 2;
wherein, on average, at least one building block (I) is attached via an SiC bond per organopolysiloxane unit of the formula (II).

5. The crosslinked organopolysiloxane according to claim 1;
wherein the crosslinked organopolysiloxane has a hydrophilic-lipophilic balance ("HLB") value of from 6 to 8.

6. A method of preparing a crosslinked organopolysiloxane according to claim 1, the method comprising:
reacting identical or different organopolysiloxanes of the formula (IIa) in a hydrosilylation reaction with a compound which has at least one hydroxy group and at least one multiple bond, and optionally compounds which have at least one multiple bond and no OH group; and
carrying out a dehydrogenative condensation with a product of the reacting step;

wherein the formula (IIa) is:

 (IIa)

where $M=(R^1R^2{}_2SiO_{1/2})$;
where $D=(R^2{}_2SiO_{2/2})$;
where $D'=(R^2R^3SiO_{2/2})$;
where $T=(R^2SiO_{3/})$;
where $Q=(SiO_{4/2})$;
where a=30 to 800;
where b=1 to 40;
where c=0 to 2;
where d=0 to 2;
where $R^1=R^2$ or $R^3$;
where $R^2$=independently of one another, V or H, or identical or different linear or branched, optionally aromatic, hydrocarbon radicals having 1 to 32 carbon atoms, which optionally carry OH or ester functions, with the proviso that $R^2$ is at least partially a hydrogen instead of V;
where $R^3$=independently of one another, identical or different polyether radicals of the general formula (III):

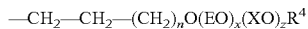 (III);

where $EO=(-C_2H_4O-)$;
where $PO=(-C_3H_6O-)$;
where $XO=(C_2H_3R^5O)$;
where n=1 to 16;
where x=2 to 50;
where y=0 to 50;
where z=0 to 10;
where $R^4$=independently of one another, identical or different radicals selected from the group consisting of H, alkyl radicals having 1 to 16 carbon atoms, and carboxylate radicals; and
where $R^5$=independently of one another, identical or different radicals selected from the group consisting of:
alkyl radicals having 2 to 16 carbon atoms, which are optionally interrupted by ether functions;
alkaryl radicals having 7-18 carbon atoms; and
aryl radicals having 6 to 16 carbon atoms;
where V=a bond to the building block of the formula I;
wherein reaction conditions are chosen such that, following the hydrosilylation, some of the Si—H bonds are furthermore present in the reaction product.

7. A method of forming an emulsion with oil and water components, the method comprising:
adding a crosslinked organopolysiloxane according to claim 1 to the water and oil components.

8. An emulsifier system for cosmetic and pharmaceutical water-in-oil emulsions comprising:
crosslinked organopolysiloxanes according to claim 1.

9. The emulsifier system according to claim 8;
wherein, besides crosslinked polysiloxanes, the emulsifier system also has uncrosslinked polysiloxanes of the formula IIb:

 (IIb);

where $M=(R^1R^2{}_2SiO_{1/2})$;
where $D=(R^2{}_2SiO_{2/2})$;
where $D'=(R^2R^3SiO_{2/2})$;
where $T=(R^2SiO_{3/2})$;
where $Q=(SiO_{4/2})$;
where a=30 to 800;
where b=1 to 40;
where c=0 to 2;
where d=0 to 2;
where $R^1=R^2$ or $R^3$;

where $R^2$=independently of one another, H, or identical or different linear or branched, optionally aromatic, hydrocarbon radicals having 1 to 32 carbon atoms, which optionally carry OH or ester functions;

where $R^3$=independently of one another, identical or different polyether radicals of the general formula (III):

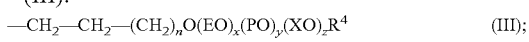 (III);

where $EO=(-C_2H_4O-)$;
where $PO=(-C_3H_6O-)$;
where $XO=(C_2H_2R^5O)$:
where n=1 to 16;
where x=2 to 50;
where y=0 to 50;
where z=0 to 10;
where $R^4$=independently of one another, identical or different radicals selected from the group consisting of H. alkyl radicals having 1 to 16 carbon atoms, and carboxylate radicals; and
where $R^5$=independently of one another, identical or different radicals selected from the group consisting of:
  alkyl radicals having 2 to 16 carbon atoms, which are optionally interrupted by ether functions;
  alkaryl radicals having 7-18 carbon atoms; and
  Aryl radicals having 6 to 16 carbon atoms.

10. The emulsifier system according to claim 8;
wherein the emulsifier system has a polydispersity of >50.

11. The emulsifier system according to claim 9;
wherein the mass ratio of crosslinked polysiloxanes II to uncrosslinked polysiloxanes IIb is from 0.8:02 to 0.2:0.8 and/or
wherein, in the compounds of the formulae II and/or IIb, polyether radicals or building blocks of the formulae I or III are present in which x/(1+y+z) is in each case>1; and/or
wherein, in the compounds of the formulae II and/or IIb, the ratio a/b is >2; and/or
wherein, in the compounds of the formulae II and/or IIb, on average, at least three polyether radicals are present and the maximum number of polyether radicals $R^3$ bonded to the molecule is less than or equal to b.

12. The emulsifier system for cosmetic and pharmaceutical water-in-oil emulsions according to claim 8;
wherein the emulsifier system has:
a hydrophilic-lipophilic balance ("HLB") value of from 4 to 10;
a polydispersity of >50; and
a mass ratio of crosslinked polysiloxanes to uncrosslinked polysiloxanes of from 0.8:0.2 to 0.2:0.8.

13. A method of forming a water-in-oil emulsion ox a dispersion, the method comprising:
adding at least one of the emulsifier systems according to claim 8 to the components of the water-in-oil emulsion or dispersion.

14. A cosmetic, dermatological, or pharmaceutical formulation comprising:
the emulsifier system according to claim 8.

15. The cosmetic, dermatological or pharmaceutical formulation of claim 14;
wherein the cosmetic, dermatological, or pharmaceutical formulation is a water-in-oil emulsion or dispersion.

16. A cosmetic, dermatological, or pharmaceutical formulation comprising:
a crosslinked organopolysiloxane according to claim 1.

17. The cosmetic, dermatological, or pharmaceutical formulation of claim 16;
wherein the cosmetic, dermatological, or pharmaceutical formulation is a water-in-oil emulsion or dispersion.

* * * * *